(12) United States Patent
Stabelfeldt et al.

(10) Patent No.: US 8,092,439 B2
(45) Date of Patent: Jan. 10, 2012

(54) ABSORBENT ARTICLE WITH WAIST RELIEF FEATURE

(75) Inventors: Sara Jane Wille Stabelfeldt, Appleton, WI (US); Connie May McMorrow, Menasha, WI (US); John Timothy Hahn, Merrill, WI (US); Thomas Harold Roessler, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 435 days.

(21) Appl. No.: 12/316,629

(22) Filed: Dec. 15, 2008

(65) Prior Publication Data

US 2010/0152694 A1 Jun. 17, 2010

(51) Int. Cl.
*A61F 13/15* (2006.01)
(52) U.S. Cl. .............................. 604/385.09; 604/385.01
(58) Field of Classification Search ............ 604/385.01, 604/385.09
See application file for complete search history.

(56) References Cited

U.S. PATENT DOCUMENTS

| | | | |
|---|---|---|---|
| 1,397,381 A | 11/1921 | Laing | |
| 4,230,113 A | 10/1980 | Mehta | |
| 4,675,015 A | 6/1987 | Brown | |
| 4,769,023 A | 9/1988 | Goebel et al. | |
| 4,917,697 A | 4/1990 | Osborn, III et al. | |
| D311,582 S | 10/1990 | Gilchrist | |
| D334,978 S * | 4/1993 | Rutherford | D24/126 |
| D341,422 S | 11/1993 | Cosentino | |
| 5,295,986 A | 3/1994 | Zehner et al. | |
| 5,358,500 A | 10/1994 | Lavon et al. | |
| 5,599,338 A | 2/1997 | Enloe | |
| 5,836,930 A | 11/1998 | Lantz et al. | |
| 6,017,406 A | 1/2000 | Vogt | |
| D452,315 S | 12/2001 | Coates | |
| 6,423,047 B1 | 7/2002 | Webster | |
| 7,361,167 B2 * | 4/2008 | Erickson et al. | 604/385.09 |
| 7,641,641 B2 * | 1/2010 | Ramshak | 604/385.01 |
| 2004/0068244 A1 | 4/2004 | Salone et al. | |
| 2006/0161124 A1 | 7/2006 | Erickson et al. | |
| 2006/0212013 A1 * | 9/2006 | Cohen et al. | 604/385.09 |
| 2006/0241558 A1 | 10/2006 | Ramshak | |
| 2006/0241559 A1 | 10/2006 | Buhrow et al. | |

FOREIGN PATENT DOCUMENTS

| | | |
|---|---|---|
| DE | 295 13 199 U1 | 4/1996 |
| EP | 1 064 896 B1 | 6/2008 |
| JP | 64-076852 A | 3/1989 |
| WO | WO 01/45622 A1 | 6/2001 |
| WO | WO 2006/078669 A1 | 7/2006 |
| WO | WO 2006/101581 A1 | 9/2006 |
| WO | WO 2006/115563 A2 | 11/2006 |

* cited by examiner

*Primary Examiner* — Lynne Anderson
(74) *Attorney, Agent, or Firm* — David J. Arteman; Sarah Ann Dressel

(57) ABSTRACT

An absorbent article includes a liquid pervious bodyside liner; a liquid impervious outer cover; and an absorbent core positioned between the bodyside liner and the outer cover. The absorbent article defining a crotch portion connected between a front portion and a back portion; the front portion includes a front waist region, a front waist edge, and a front waist relief area. The front waist relief area is defined in part by a first material cut edge and a second material cut edge wherein the second material cut edge extends beyond the first material cut edge to define a fringe.

18 Claims, 21 Drawing Sheets

ABSORBENT ARTICLE WITH WAIST RELIEF FEATURE

BACKGROUND OF THE INVENTION

The umbilical cord of newborn infants is a very sensitive area during the first weeks of life. Doctors recommend minimizing contact with this area during the healing process. As such, some absorbent articles have been provided with a cutout in the front portion of the article to accommodate the umbilical cord area. However, some of the currently available cutouts may have stiff edges that may occasionally rub against the umbilical cord. Thus, there is a need for a waist relief feature having a soft edge to minimize irritation and a need for a method to make said feature.

SUMMARY OF THE INVENTION

In one aspect, the present invention provides an absorbent article having a liquid pervious bodyside liner, a liquid impervious outer cover, and an absorbent core positioned between the bodyside liner and the outer cover. The absorbent article has a crotch portion connected between a front portion and a back portion. The front portion includes a front waist region, a front waist edge, and a front waist relief area. The front waist relief area is defined in part by a first material cut edge and a second material cut edge. The first material cut edge defines a first relief depth of at least 10 mm and the second material cut edge defines a second relief depth wherein the second relief depth is at least 3 mm less than the first relief depth.

In various embodiments, the first material may be the outer cover and the second material may be the liner. In some embodiments, the first material may be the outer cover and the second material may be a waist elastic. In some embodiments, the first material may be the outer cover and the second material may be an outer cover facing material. In some embodiments, the first material may be the outer cover and the second material may be the fastener landing material.

In some embodiments, the front waist relief area defines a width and the second material cut edge extends beyond the first material cut edge by the same amount along substantially the entire width of the front waist relief area. In some embodiments, the first material has a first relief depth of at least 20 mm and a first relief width of at least 60 mm. In some embodiments, the second material has a second relief depth of less than 3 mm.

In some embodiments, the second material cut edge extends beyond the first material cut edge to define a fringe and the fringe includes an anchor tab joined thereto.

In some embodiments, the back waist region includes a back waist relief area. The back waist relief area is defined in part by a first material back cut edge and a second material back cut edge wherein the first material back cut edge defines a first back relief depth and the second material back cut edge defines a second back relief depth wherein the second back relief depths is at least 3 mm less than the first back relief depth.

In some embodiments, the front waist relief area defines a width and the second material cut edge extends beyond the first material cut edge by the same amount along substantially the entire width of the front waist relief area and the second material has a second material back relief depth of less than 3 mm in the back waist relief area.

In another aspect, the present invention provides an absorbent article having a liquid pervious bodyside liner, a liquid impervious outer cover, and an absorbent core positioned between the liner and the outer cover. The absorbent article has a crotch portion connected between a front portion and a back portion. The front portion includes a front waist region, a front waist edge, and a front waist relief area. The front waist relief area is defined in part by a first material cut edge and a second material cut edge. The first material cut edge has a first relief depth of at least 20 mm, the second material cut edge has a second relief depth of at least 10 mm, and the second relief depth is at least 3 mm less than the first relief depth. In this aspect, the first material includes the outer cover and the second material includes a front waist elastic joined to the front waist region.

In some embodiments, the front waist relief area defines a width and the second material cut edge extends beyond the first material cut edge to define a fringe wherein the fringe extends beyond the first material cut edge by the same amount along substantially the entire width of the front waist relief area.

In some embodiments, the back portion may include a back waist region, a back waist edge, and a back waist relief area. The back waist relief area is defined in part by a first material back cut edge and a second material back cut edge. The first material back cut edge has a relief depth of at least 10 mm in the back waist relief area. The second material back cut edge has a relief depth of less than 3 mm.

In some embodiments, the front waist relief area defines a width and the second material front cut edge extends beyond the first material front cut edge by the same amount along substantially the entire width of the front waist relief area.

In some embodiments, the second cut edge of the front waist elastic extends beyond the first cut edge of the outercover, outercover facing, and liner.

Another aspect of the present invention provides an absorbent article having a liquid pervious bodyside liner, a liquid impervious outer cover, and an absorbent core positioned between the liner and the outer cover. The absorbent article defines a crotch portion connected between a front portion and a back portion. The front portion includes a front waist region, a front waist edge, and a front waist relief area. The front waist relief area is defined in part by a first material front cut edge and a second material front cut edge. The back waist relief area is defined in part by the first material back cut edge and the second material back cut edge. The first material front cut edge has a first front relief depth of at least 20 mm, the second material front cut edge has a second front relief depth of at least 10 mm and the second front relief depth is at least 3 mm less than the first front relief depth. The first material back cut edge has a first back relief depth of at least 5 mm. The first material is the outer cover and the second material is a waist elastic.

In some embodiments, the second material front cut edge extends beyond the front cut edge of the outercover, outercover facing, and liner at a longitudinal centerline.

In some embodiments, the front waist relief area defines a width and the second material front cut edge extends beyond the first material front cut edge to define a front fringe. The front fringe extends beyond the first material front cut edge by the same amount along substantially the entire width of the front waist relief area.

DETAILED DESCRIPTION OF THE DRAWINGS

The waist relief features of the present invention may be useful for providing relief to the healing umbilical area of newborns and/or increasing comfort in the waist portions and/or increasing retraction in the waist portions of various absorbent articles. The absorbent articles of the present invention will be described in terms of diapers adapted to be worn by babies, particularly newborns, about the lower torso. However, the absorbent articles of the present invention may also be applicable to other articles such as adult incontinent absorbent articles, training pants, feminine care absorbent articles and the like.

Figure 1:
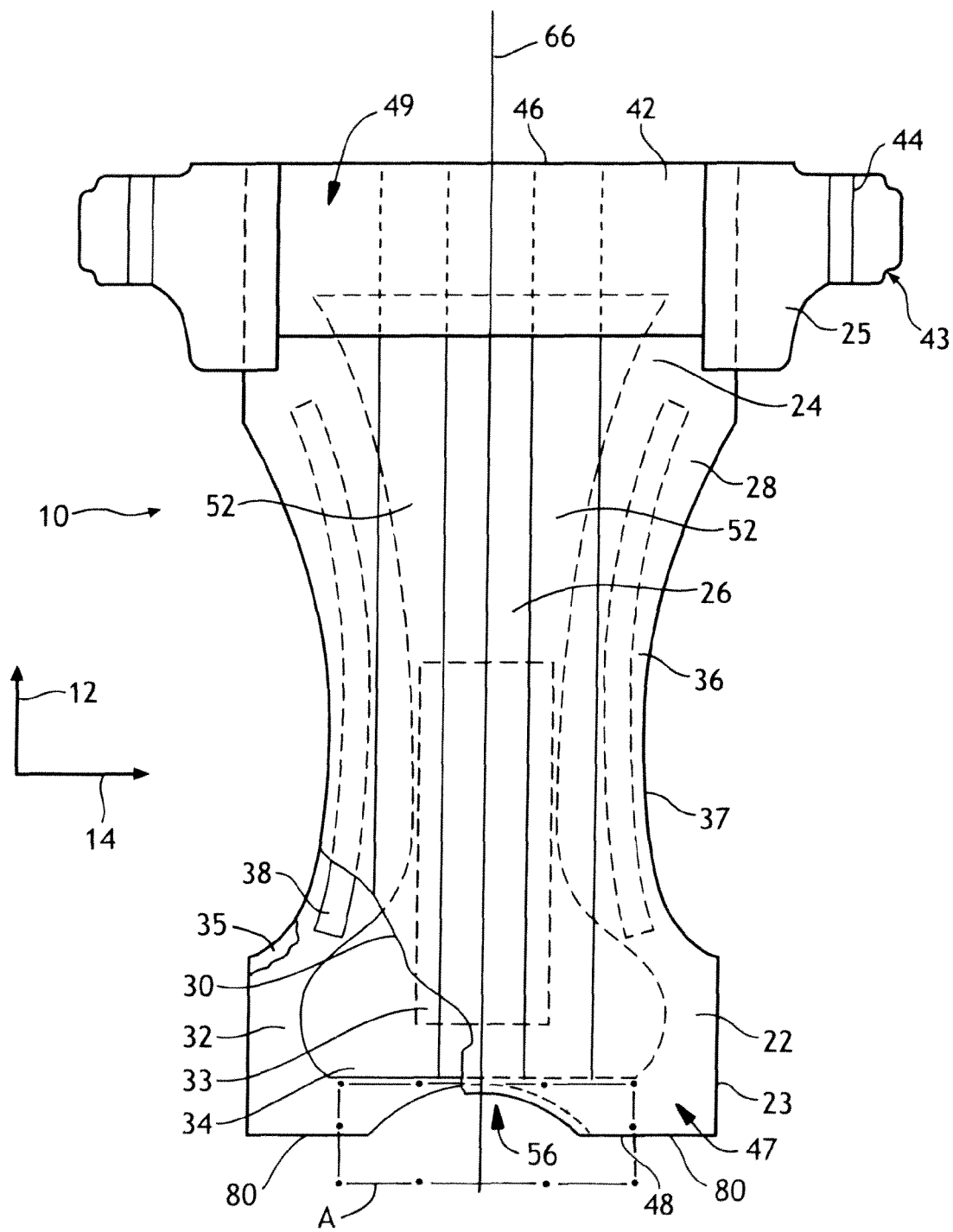
FIG. 1 representatively illustrates a partially cut away, top plan view of an absorbent article in a stretched and laid flat condition with the surface of the article that contacts the skin of the wearer facing the viewer.

FIG. 1 representatively illustrates a diaper 10 of the present invention in an unfastened condition. Portions of the diaper 10 are cut away to illustrate underlying structures. The surface of the diaper which contacts the wearer is facing the viewer in FIG. 1. The diaper 10 has a longitudinal direction 12 and a lateral direction 14. In the longitudinal direction 12, the diaper 10 defines a front portion 22, a back portion 24, and a crotch portion 26 connecting the front portion 22 and the back portion 24. The diaper 10 includes a bodyside liner 30, an outer cover 32 and an absorbent core 34 located between the bodyside liner 30 and the outer cover 32. The front portion 22 may include, at least partially, one or more front ears 23. The back portion 24 may include, at least partially, one or more back ears 25. The front ears 23 and/or the back ears 25 may be formed from extensions of the bodyside liner 30, the outer cover 32, combinations of both the bodyside liner 30 and the outer cover 32, or by the addition of one or more separate components as is known in the art.

The diaper 10 may also include a fastener system 43. The fastener system 43 may include one or more back fasteners 44 and one or more front fasteners 45 (see FIG. 2 for example). Portions of the fastener system 43 may be included in the front portion 22, the back portion 24, or both. The fastener system 43 is adapted to secure the diaper 10 about the waist of a wearer and maintain the diaper 10 in place during use.

The diaper 10 may also include a surge portion 33 joined to the absorbent core 34 and/or the bodyside liner 30. As used herein, reference to a front portion 22 refers to that part of the diaper which is generally located on the front of a wearer when in use. Reference to the back portion 24 refers to the portion of the diaper generally located at the back of the wearer when in use, and reference to the crotch portion 26 refers to that portion which is generally located between the legs of the wearer when in use.

The crotch portion 26 has opposite longitudinal side portions 28 which may include a pair of elasticized, longitudinally-extending leg cuffs 36. The leg cuffs 36 are generally adapted to fit about the legs of a wearer in use and serve as a mechanical barrier to the lateral flow of body exudates. The leg cuffs 36 may be elasticized by a pair of leg elastics 38. The diaper 10 may further include a front waist elastic 40 (see FIG. 5 for example) and/or a back waist elastic 42.

The back portion 24 may have a straight back waist edge 46, an arcuate back waist edge 46, or a back waist edge 46 cut in other shapes as are known in the art. The front portion 22 may have a straight front waist edge 48, an arcuate front waist edge 48, or a front waist edge 48 cut in other shapes as are known in the art. As used herein, the term "straight" refers to edges or portions of edges that are substantially free from curves, bends, angles, notches or irregularities. For example, the back waist edge 46 of FIG. 1 is a straight edge whereas, the front waist edge 48 has two straight portions divided by an arcuate portion.

The diaper 10 may also include a pair of containment flaps 52 that may extend longitudinally along the diaper 10 and may also be adapted to provide a barrier to the flow of body exudates. It should be recognized that individual components of the diaper 10 may be optional depending upon the intended use of the diaper 10.

The bodyside liner 30 of the diaper 10, as representatively illustrated in FIG. 1, suitably presents a body facing surface which is intended to be worn adjacent the body of the wearer and is compliant, soft feeling and nonirritating to the wearer's skin. Further, the bodyside liner 30 may be less hydrophilic than the absorbent core 34 and may be sufficiently porous to be liquid permeable. A suitable bodyside liner 30 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 30 is suitably employed to help isolate the wearer's skin from fluids held in the composite absorbent core 34.

Figure 2:
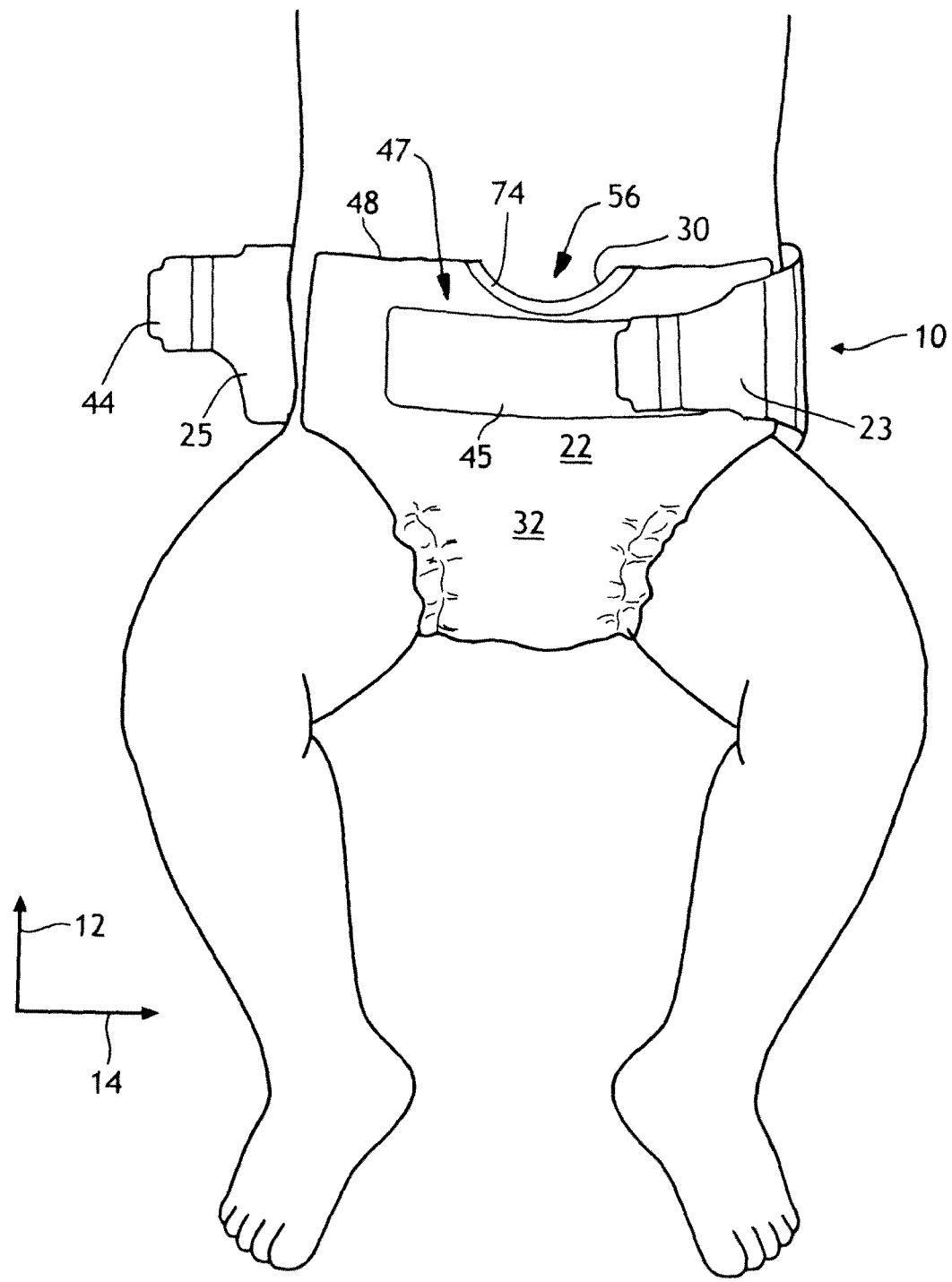
FIGS. 2, 7, 10, and 11 representatively illustrate front perspective views of exemplary embodiments of absorbent articles of the present invention partially fastened about the waist and legs of a wearer.

The outer cover 32 of the diaper 10, as representatively illustrated in FIG. 2, suitably presents a garment facing surface which is intended to be worn adjacent the clothing of the wearer. The outer cover 32 may include a polyethylene film. Alternative constructions of the outer cover 32 may comprise a woven or non-woven fibrous web layer which has been totally or partially constructed or treated to impart a desired level of liquid impermeability to selected regions of the outer cover that are adjacent or proximate the absorbent core 34. For example, a clothlike outer cover may be composed of polypropylene spunbond fabric which is laminated and thermally bonded to a stretch-thinned polypropylene film. In such embodiments, the polypropylene spunbond fabric may be referred to as the outer cover facing material 35 and the polypropylene film may be referred to as the outer cover material 32. In other embodiments, the woven or non-woven fibrous web layers and other layers may be collectively referred to as the outer cover. The outer cover 32 may optionally include a micro-porous, "breathable" material which permits vapors to escape from diaper 10 while still preventing liquid exudates from passing through. For example, the outer cover 32 may be composed of a microporous polymer film or a nonwoven fabric which has been coated or otherwise treated to impart a desired level of liquid impermeability. The outer cover 32 can also be embossed or otherwise provided with a matte finish to exhibit a more aesthetically pleasing appearance. The size of outer cover 32 is typically determined by the size of diaper 10 and the exact diaper design selected.

The bodyside liner 30 and outer cover 32 are generally joined in facing relationship with the absorbent core 34 located therebetween. The bodyside liner 30 and the outer cover 32 may be joined to each other around the outer periphery of the diaper 10 by any means known to those skilled in the art such as adhesive bonds, sonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

The leg cuffs 36 are suitably formed by portions of the outer cover 32, and/or bodyside liner 30, which extend beyond the longitudinal sides of the absorbent core 34. Alternatively, the leg cuffs 36 can be formed from separate materials joined to the outer cover 32 and/or bodyside liner 30. In some embodiments, the leg cuffs 36 may have an arcuate shape resulting from a leg cut out 37. In other embodiments, the leg cuffs 36 may have a generally straight leg cut out 37.

The leg cuffs 36 may include leg elastics 38. Front waist elastics 40 and/or back waist elastic 42 may also be provided. The leg elastics 38 may be arranged to draw and hold the diaper 10 against the legs of the wearer. The waist elastics 40 and 42 may also be arranged to draw and hold the diaper 10 against the wearer, particularly at the waist. Materials suitable for use in forming leg elastics 38 and/or waist elastics 40 and 42 are known to those skilled in the art. Exemplary of such materials are strands or ribbons of a polymeric, elastomeric material which are adhered to the diaper 10 in a stretched position, or which are attached to the diaper while the diaper is pleated, such that elastic constrictive forces are imparted to the diaper 10. The leg elastics 38 and/or waist elastics 40 and 42 may have any configuration which provides the desired performance. The leg elastics 38 may be generally straight or optionally curved to more closely fit the contours of the legs and buttocks of the wearer and better contain bodily exudates. The leg elastics 38 and/or waist elastics 40 and 42 may be attached to the diaper 10 in any of several ways which are well known to those skilled in the art. For example, the elastics may be joined to the diaper 10 by ultrasonic bonding, thermal bonding, adhesive bonding, and the like, and combinations thereof.

The front ears 23 and/or the back ears 25 are suitably formed by portions of the outer cover 32, and/or bodyside liner 30, which extend beyond the longitudinal sides of the absorbent core 34. For example, in FIG. 1, the front ears 23 are illustrated as portions of both the outer cover 32 and the bodyside liner 30. Alternatively, the front ears 23 and/or back ears 25 may be formed from separate materials which are joined to the outer cover 32 and/or bodyside liner 30. For example, in FIG. 1, the back ears 25 are illustrated as separate pieces of material attached to the bodyside liner 30.

The front ears 23 and/or the back ears 25 of the present invention may comprise one or more materials joined together to form a composite ear as is well known in the art. One or more of the materials may be elastomeric. Elastomeric ears can be formed from any type of an elastomeric material capable of performing as described herein. Generally, the elastomeric material will be stretchable in at least one direction. Preferably, the elastomeric material will be stretchable in two directions. When the elastomeric material is stretchable in a single direction, the stretch direction of the elastomeric material will be oriented so as to provide elastomeric forces which tend to pull the front and back portions of the diaper towards one another such that the diaper is maintained about the waist of a wearer.

The elastomeric material may be an inherently elastomeric material, that is, one which is formed in an elastomeric state, or may be rendered elastomeric through processing subsequent to formation. For example, the elastomeric material may be heat or pressure activated. In particular embodiments of the invention, portions of the ears may comprise an elastomeric material, such as a stretch-bonded-laminate (SBL) material, a neck-bonded-laminate (NBL) material, an elastomeric film, an elastomeric foam material, or the like, or combinations thereof.

In some embodiments, the back fasteners 44 may be joined to the back portion 24, the back ears 25 or both and the front fasteners 45 may be joined to the front portion 22, the front ears 23, or both. The back fasteners 44 may be one or more discrete pieces of material joined to the diaper 10 and adapted to align with and work in conjunction with the front fasteners 45, which may be one or more discrete pieces of material joined to the diaper 10. For example, the front fastener 45 may be a piece of loop material joined with the outer cover 32 in the front portion 22 and configured to engage hook-type back fasteners 44 when the diaper 10 is wrapped about the waist and legs of a user.

Alternatively, the one or more front fasteners 45 may include portions of the outer cover 32, the bodyside liner 30, or both and be configured to engage hook-type back fasteners 44. For example, the outer cover 32 may be configured to include a non-woven material suitable for engagement with hook materials. In such an embodiment, hook-type fasteners 44 may be located at the back ears 25 and wrapped around the waist of the wearer. The hook-type fasteners 44 may then be engaged directly with the nonwoven outer cover 32 to join the back portion 24 with the front portion 22 and secure the diaper 10 about the waist of the wearer.

Alternatively, the one or more front fasteners 45 may include hook-type fasteners and the one or more back fasteners 44 may include one or more complementary loop-type fasteners. In various embodiments, the one or more back fasteners 44 and/or the one or more front fasteners 45 may comprise any suitable materials adapted to join the back portion 24 to the front portion 22 of the diaper 10 thus securing the diaper about the waist of a wearer. Suitable fastening materials include hook and loop materials, adhesives, adhesive tapes, cohesives, snaps, buttons, latches, hooks, and the like, and combinations thereof. In some embodiments both the front portion 22 and/or the back portion 24 may include dual fasteners as is known in the art.

The absorbent core 34 is positioned between the bodyside liner 30 and the outer cover 32 to form the diaper 10. The absorbent core 34 is generally conformable and capable of absorbing and retaining body exudates. The absorbent core 34 may include superabsorbent material, staple fibers, binder fibers, and the like, and combinations thereof as is known in the art. The absorbent core 34 may have any of a number of shapes and sizes. For example, the composite absorbent core may be rectangular, I-shaped or T-shaped. The size and absorbent capacity of the absorbent core 34 should be compatible with the size of the intended wearer and the fluid loading imparted by the intended use of the diaper.

In various embodiments, the surge portion 33 serves to quickly collect and temporarily hold discharged fluids and then to eventually release the fluids into the absorbent core 34. Various woven and nonwoven materials can be used to construct the surge portion 33. For example, the surge portion 33 may be a layer of a spunbonded or meltblown web of polyolefin fibers. The surge portion 33 may also be a bonded carded web of natural and synthetic fibers. The surge portion 33 may be a substantially hydrophobic material and, optionally, can be treated with a surfactant or otherwise to impart a desired level of wettability and hydrophilicity.

Containment flaps 52 may be connected to the bodyside liner or other components as is well known in the art. Suitable configurations of the containment flaps 52 are described, for example, in U.S. Pat. No. 5,599,338 issued Feb. 4, 1997, to K. Enloe, the entirety of which is incorporated herein by reference where not contradictory.

Referring again, to FIG. 1, the front portion 22 of the diaper 10 includes a front waist region 47 defined in part by the front waist edge 48. Likewise, the back portion 24 of the diaper 10 includes a back waist region 49 defined in part by the back waist edge 46. In various embodiments, the front waist region 47 and/or the back waist region 49 may include a front waist relief area 56 and/or a back waist relief area 58 (See for example, FIG. 8) respectively.

As used herein, the term "waist relief area" describes a portion of the front waist region and/or the back waist region wherein a portion of one or more materials has been removed proximate the waist edge. Waist relief areas may be utilized to minimize contact with the healing umbilical area of newborns and/or provide a soft edge proximate the healing umbilical area and/or generally increase comfort in the waist regions and/or increase the retractive forces in the waist regions of various absorbent articles.

Figure 1A:
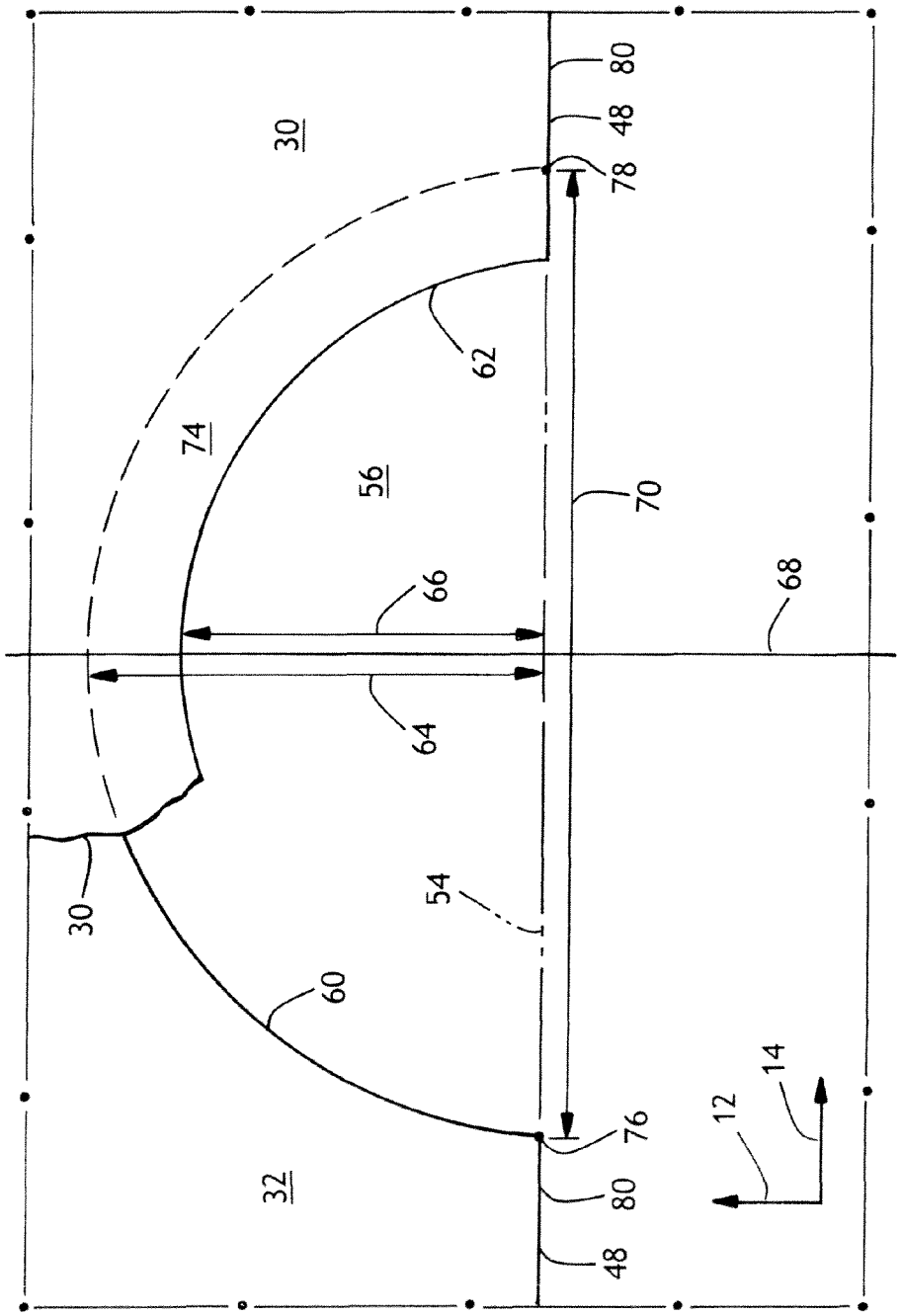
FIG. 1A representatively illustrates an enlarged view of the area designated "A" in FIG. 1.

To better illustrate the details of an exemplary waist relief area, a portion of FIG. 1, identified as "A", is enlarged and illustrated in FIG. 1A. Referring now to FIGS. 1 and 1A, the front waist relief area 56 is defined in part by a first material cut edge 60 and a second material cut edge 62. In the illustrated embodiment, the first material is the outer cover 32 and the second material is the bodyside liner 30. The first material cut edge 60 defines a first relief depth 64 and the second material cut edge 62 defines a second relief depth 66. The cut edges 60 and 64 extend to different lengths in the waist relief area 56 to provide a soft edge. In other words, in this embodiment, the liner cut edge 62 extends past the outer cover cut edge 60 to provide a fringe 74 in the waist relief area 56. In various embodiments, the second relief depth 66 is at least 3 mm, at least 4 mm, at least 5 mm, at least 6 mm, at least 7 mm, at least 8 mm, at least 9 mm, or at least 10 mm less than the first relief depth 64. Thus, in various embodiments, the fringe 74 may be at least 3 mm, at least 4 mm, at least 5 mm, at least 6 mm, at least 7 mm, at least 8 mm, at least 9 mm, or at least 10 mm in length as measured from the first cut edge 60 to the second cut edge 62.

As used herein, the term "relief depth" refers to the distance from a respective material cut edge 60 or 62 to the extended waist edge 54 and is measured at the longitudinal centerline 68. For example, referring to FIG. 1A, the first relief depth 64 is the distance from the first material cut edge 60 to the extended waist edge 54 as measured at the longitudinal centerline 68. Likewise, the second relief depth 66 is the distance from the second material cut edge 62 to the extended waist edge 54 when measured at the longitudinal centerline 68.

In various embodiments, the first relief depth 64 may be at least 10 mm, at least 20 mm, at least 30 mm, or at least 40 mm. In various embodiments, the second relief depth 66 may be less than 30 mm, less than 20 mm, or less than 10 mm. In some embodiments, the second relief depth 66 may be 0 mm. In these embodiments, the second cut edge 62 extends all the way to the front waist edge 48 and/or the back waist edge 46 (see FIG. 9 for example).

As used herein, the term "extended waist edge" refers to the imaginary line 54 intersecting the longitudinal centerline 68 and connecting one straight portion of a waist edge to another straight portion of the same waist edge. For example, FIG. 1A illustrates an extended waist edge 54 connecting one straight portion of front waist edge 48 to another straight portion of front waist edge 48.

As used herein, the term "straight" describes waist edges or portions of waist edges that are generally parallel with the lateral direction 14 and generally perpendicular with the longitudinal direction 12. For example, in FIG. 1, the back waist edge 46 is a straight waist edge and the front waist edge 48 includes two straight portions 80 on either side of the front waist relief area 56.

As used herein, the term "relief width" describes the distance, as measured in the lateral direction 14, between the points wherein the first material cut edge 60 intersects the straight portion of the front waist edge 48 or the back waist edge 46. For example, in FIG. 1A, the relief width 70 is illustrated as the distance between a first point 76 and a second point 78. The first point 76 is defined by the first intersection of the first material cut edge 60 and the straight portion 80 of the front waist edge 48. The second point 78 is defined by the second intersection of the first material cut edge 60 and the straight portion 80 of the front waist edge 48. The relief width 70 may be any suitable distance. For example, in some embodiments, the relief width 70 may be at least 25 mm, at least 30 mm, at least 40 mm, at least 50 mm, or at least 60 mm. In some embodiments, the relief width 70 may be at least 30%, at least 40%, or at least 50% the total length of the front waist edge 48 and/or back waist edge 46, as measured in the lateral direction 14. In some embodiments, the relief width 70 may be less than 90%, less than 80%, or less than 70% the length of the front waist edge 48 and/or back waist edge 46, as measured in the lateral direction 14.

Figure 3:
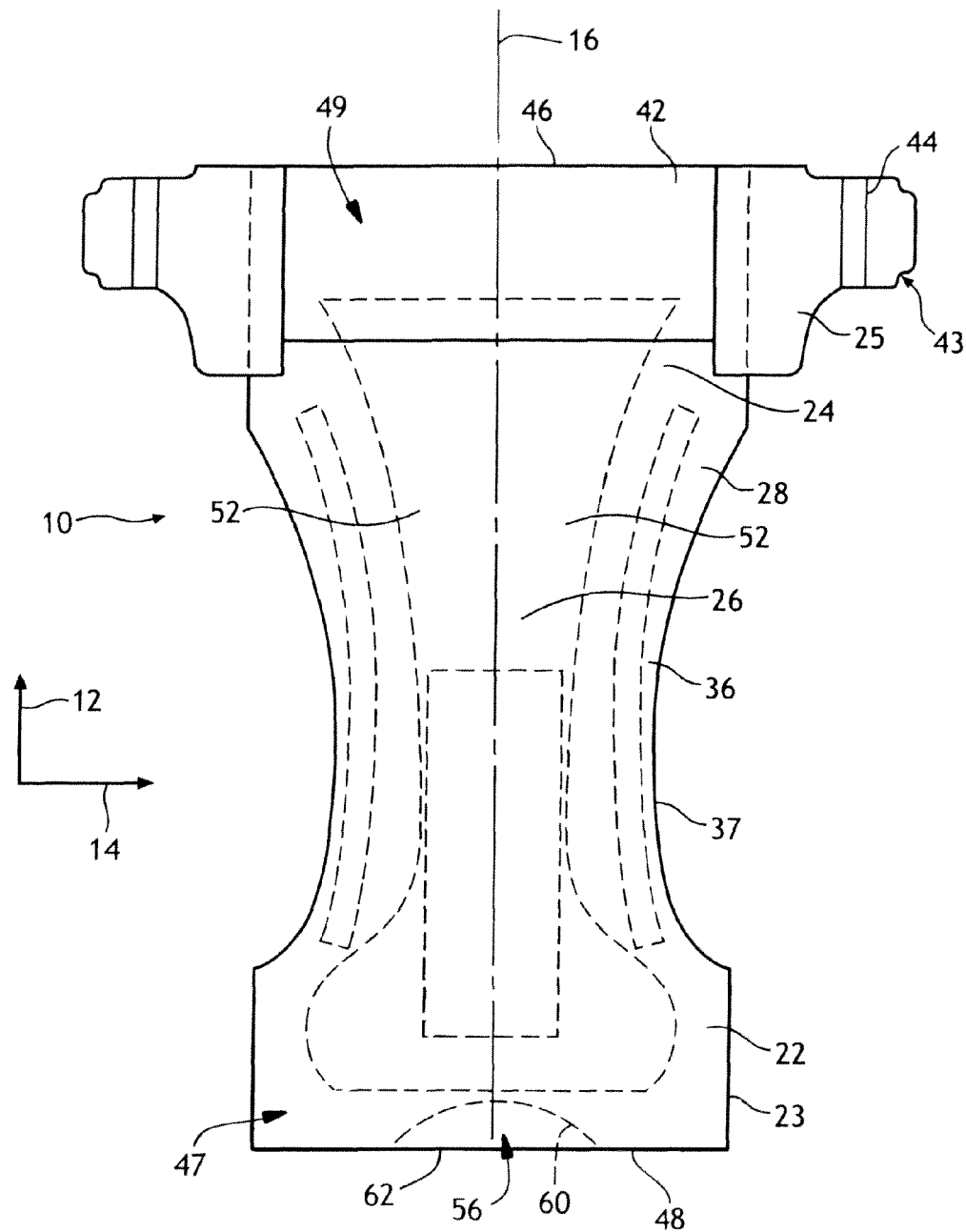
FIGS. 3-6 and 8-9A representatively illustrate top plan views of exemplary embodiments of absorbent articles of the present invention in a stretched and laid flat condition with the surface of the articles that contact the skin of the wearer facing the viewer.

In various embodiments, the first material and the second material that define the front waist relief area 56 and/or the back waist relief area 58 may be any suitable materials. Likewise, the fringe 74 in the front waist relief area 56 and/or back waist relief area 58 may be made of any suitable material or materials. For example, the fringe 74 may be composed of the bodyside liner 30, the front waist elastic 40, the back waist elastic 42, the front fastener material 45, the outer cover facing material 37, or combinations thereof. Additionally, the fringe 74 may extend beyond the cut edge of the bodyside liner 30, the front waist elastic 40, the back waist elastic 42, the front fastener material 45, the outer cover facing material 37, the outer cover material 32, or combinations thereof. For example, the absorbent article 10 illustrated in FIG. 1 includes the outer cover 32 as the first material and the bodyside liner 30 as the second material. As illustrated, the cut edge 62 of the bodyside liner 30 extends past the cut edge 60 of the outer cover 32 to create the fringe 74. In some embodiments, the cut edge 62 of the bodyside liner 30 may extend all the way to the front waist edge 48 as illustrated in FIG. 3.

Figure 4:
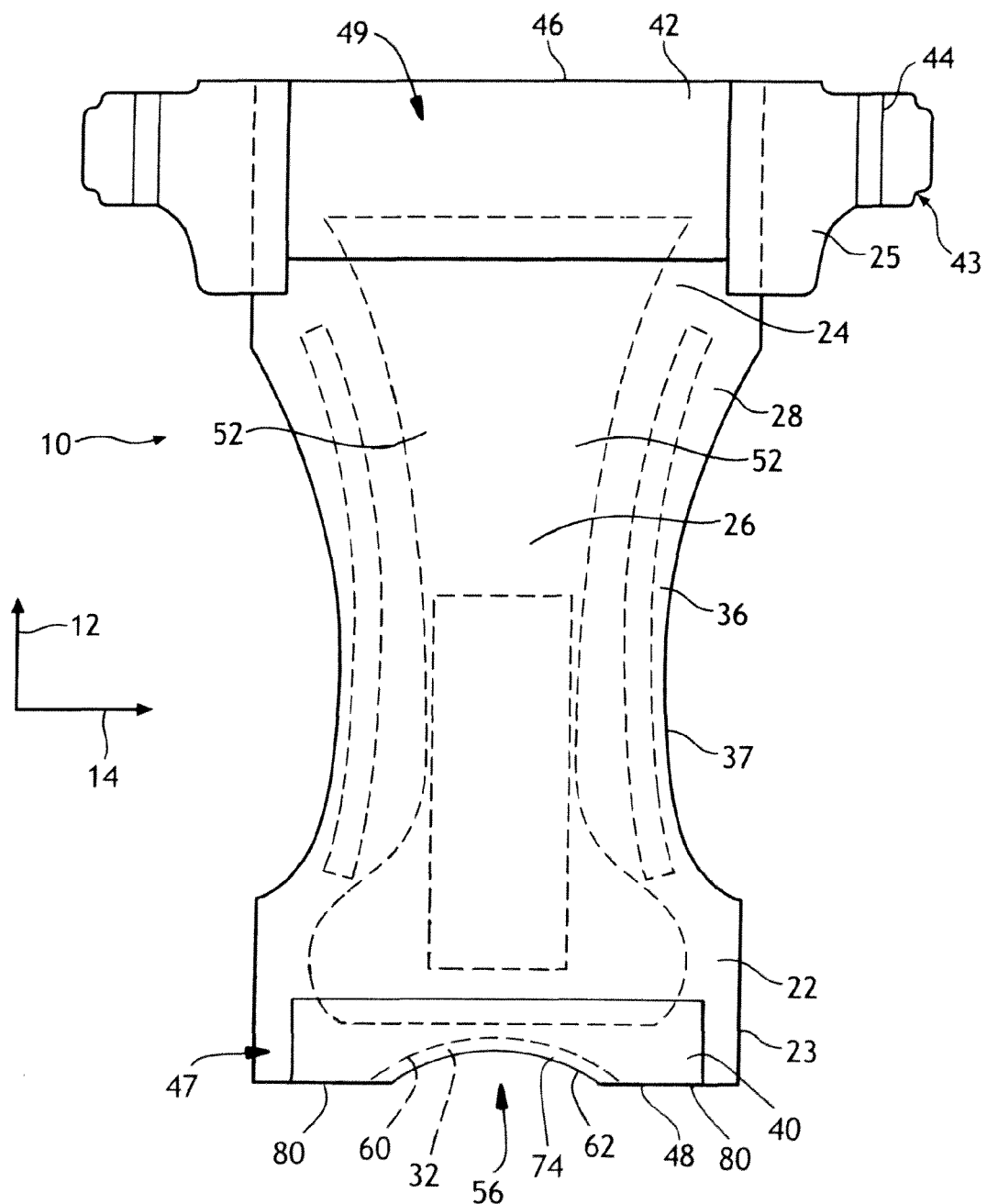
Figure 5:
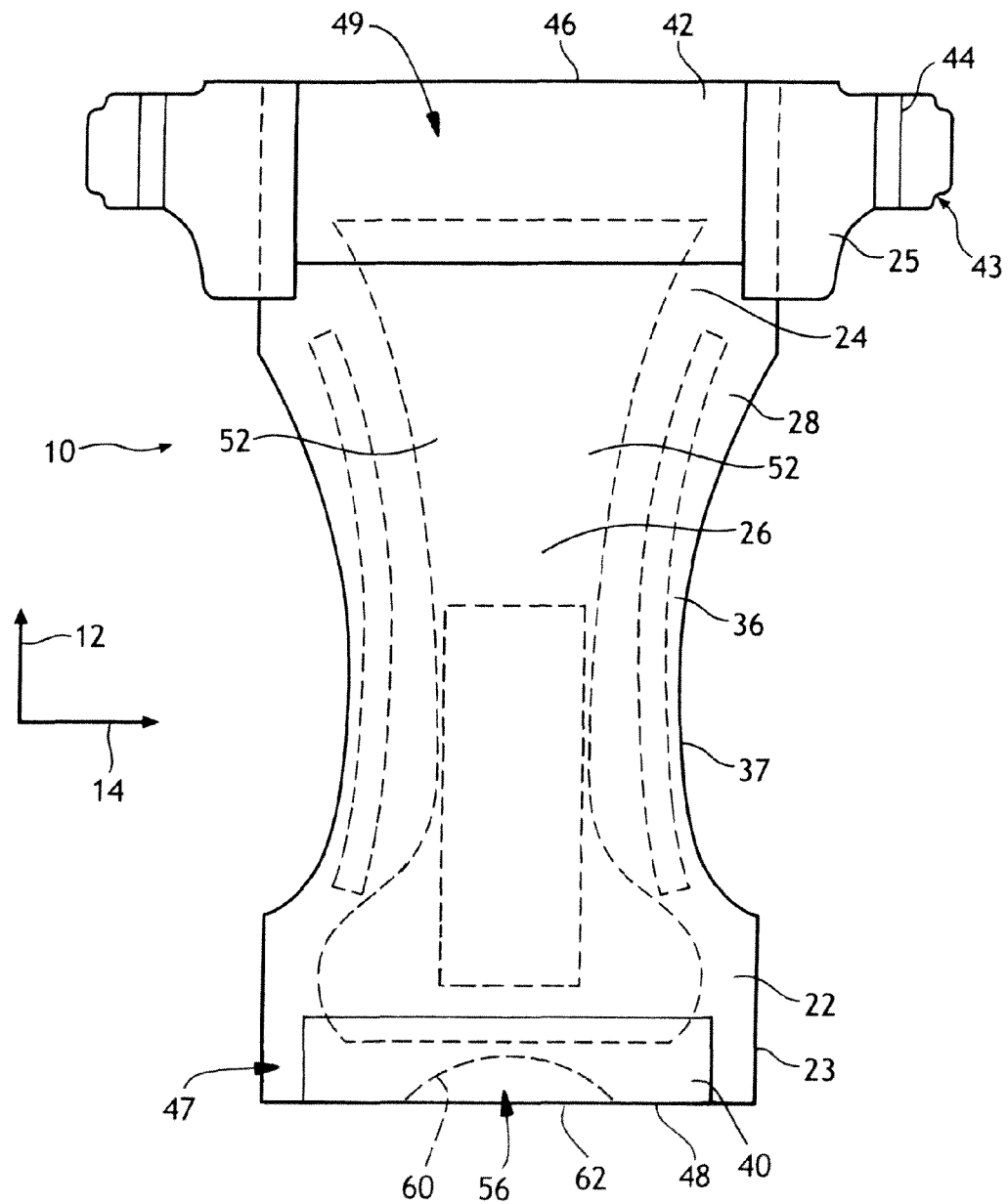

Referring now to FIG. 4, an absorbent article 10 is illustrated in an unfastened condition. The surface of the diaper 10 which contacts the wearer is facing the viewer in this illustration. The diaper 10 of FIG. 4 includes a front waist relief area 56 defined in part by a first material cut edge 60 and a second material cut edge 62 wherein the first material is the outer cover 32 and the second material is the front waist elastic 40. In the illustrated embodiment, the cut edge 62 of the front waist elastic 40 extends beyond the cut edge 60 of the outer cover 32 to create a fringe 74. In some embodiments, the cut edge 62 may also include the bodyside liner 30. In these embodiments, the front waist elastic 40 and the bodyside liner 30 would both extend beyond the cut edge 60 of the outer cover 32 to define the fringe 74. In yet other embodiments, the cut edge 62 of the front waist elastic 40 may extend all the way to the front waist edge 48 as illustrated in FIG. 5. In some embodiments, the cut edge 62 may also include the bodyside liner 30 wherein both the bodyside liner 30 and the front waist elastic 40 extend all the way to the front waist edge 48 in the front waist relief area 56.

Figure 6:
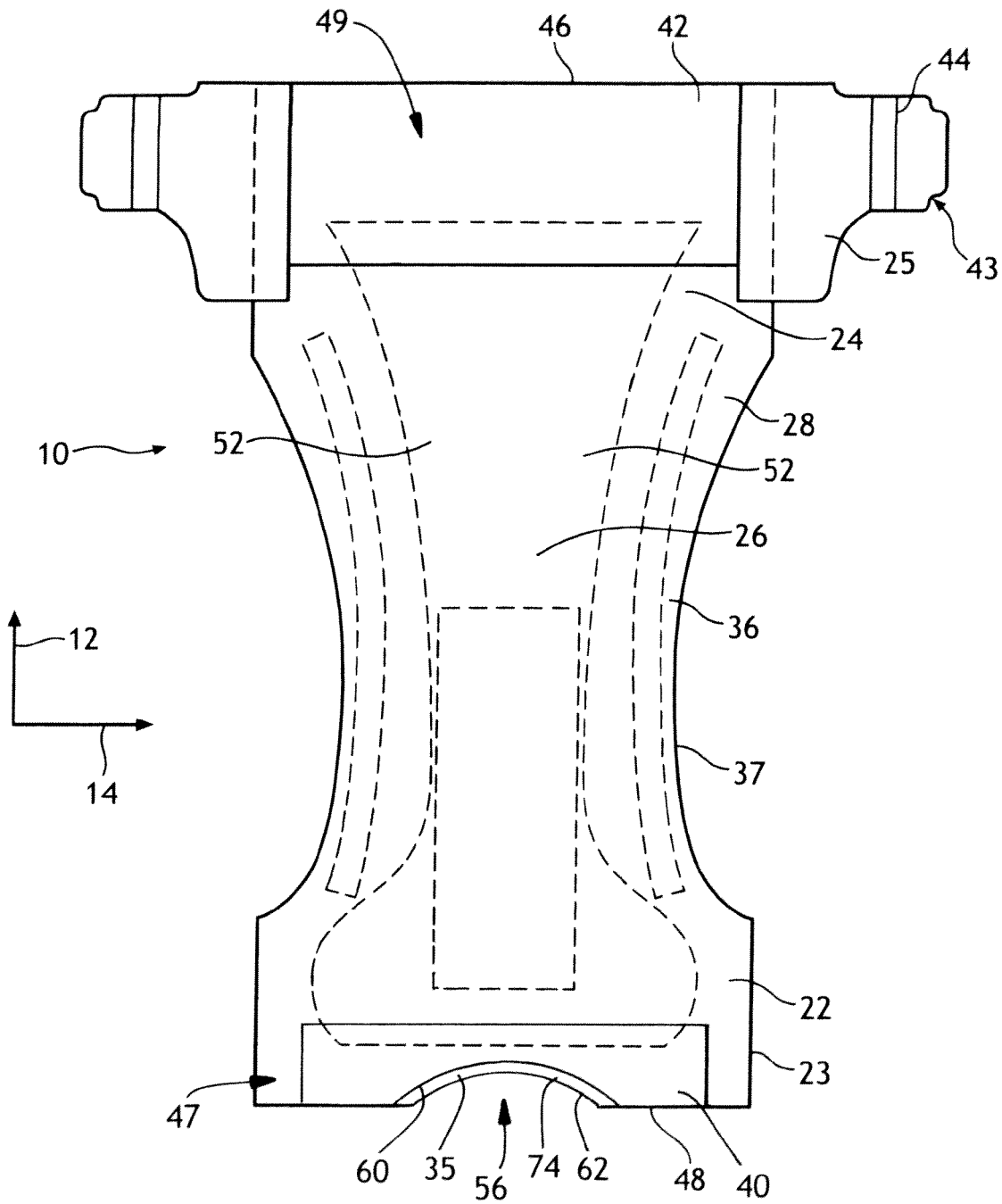

In some embodiments, the front waist relief area 56 and/or back waist relief area 58 may be defined in part by a first material cut edge 60 and second material cut edge 62 wherein the first material includes the outer cover material 32 and the second material includes an outer cover facing material 35. For example, as illustrated in FIG. 6, an absorbent article 10 includes a front waist relief area 56 defined in part by a first cut edge 60 and second cut edge 62. The outer cover facing material 35 extends beyond the outer cover material 32 to define the fringe 74 in a portion of the front waist relief area 56.

Figure 7:
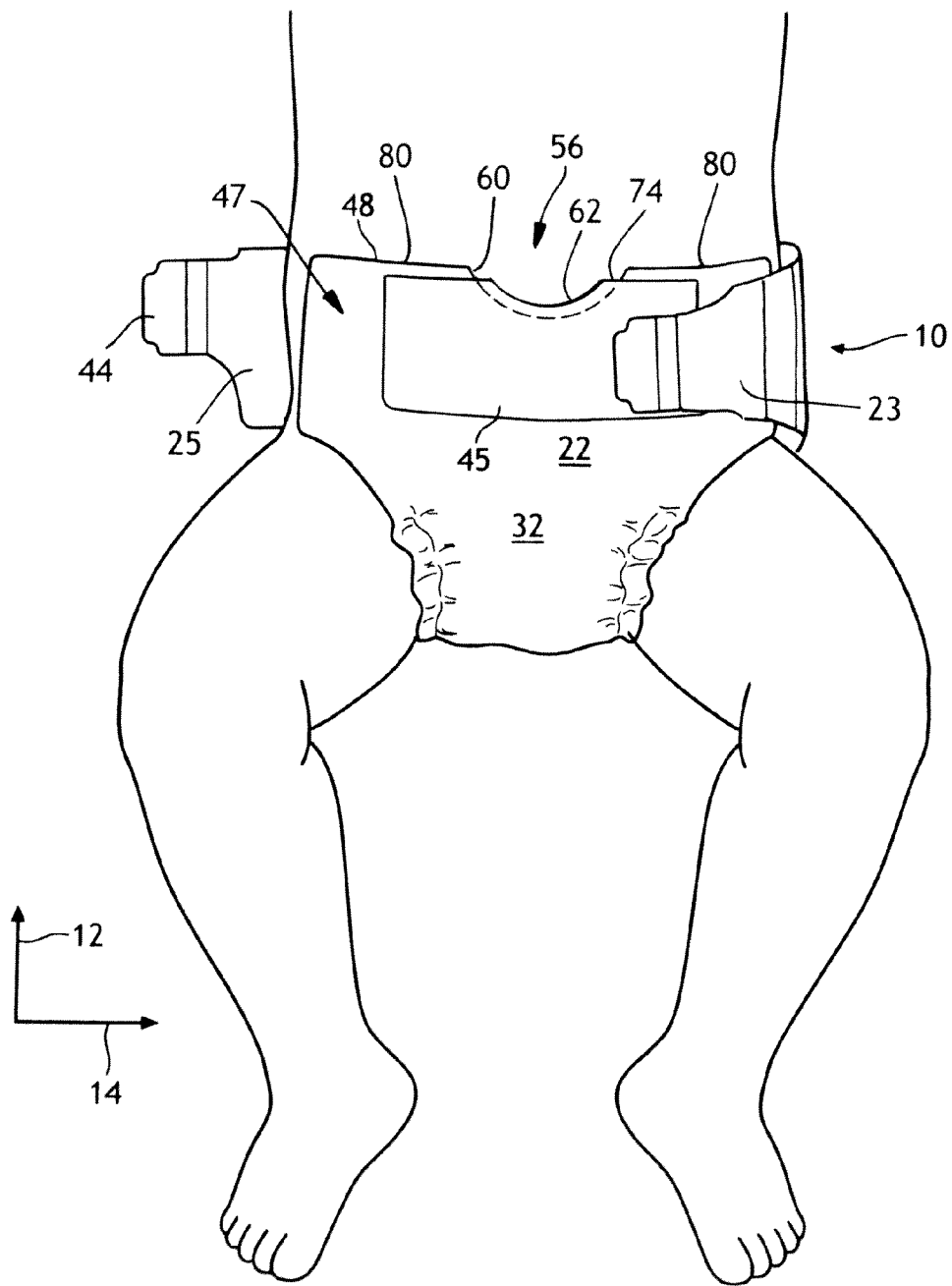

In some embodiments, the front waist relief area 56 and/or the back waist relief area 58 may be defined in part by a first material cut edge 60 and a second material cut edge 62 wherein the first material includes the outer cover material 32 and the second material includes a fastener material. For example, as illustrated in FIG. 7, an absorbent article 10 includes a front waist relief area 56 defined, in part, by a first cut edge 60 of the outer cover 32 and a second cut edge 62 of the front fastener material 45. The front fastener material 45 extends beyond the cut edge of the outer cover material 32 to define the fringe 74.

In various embodiments, the first material and/or the second material that define the front waist relief area 56 and/or the back waist relief area 58 may extend all the way to the front waist edge 48 and/or the back waist edge 46 of the diaper 10 in areas outside the front waist relief area 56 and/or back waist relief area 58. For example, as illustrated in FIG. 4, the outer cover 32 is the first material and extends to the front waist edge 48 in areas 80 outside the waist relief area 56. Likewise, the front waist elastic 40 is the second material and extends to the front waist edge 48 in areas 80 outside the waist relief area 56. In some embodiments, the first material and/or the second material that define the front waist relief area 56 and/or the back waist relief area 58 may not extend all the way to the front waist edge 48 and/or the back waist edge 46 of the diaper 10 in areas 80 outside the front waist relief area 56 and/or back waist relief area 58. For example, as illustrated in FIG. 7, the outer cover 32 is the first material and extends to the front waist edge 48 in areas 80 outside the waist relief area 56. In contrast, the fastener material 45 is the second material and does not extend to the front waist edge 48 in areas 80 outside the waist relief area 56. In these situations, the relief depth of the fastener material 45 is the distance from the extended waist edge 54 of the outer cover 32 to the material cut edge of the fastener material 45 as measured at the longitudinal centerline 68, not the extended waist edge 54 of the fastener material 45.

In various embodiments, the second material cut edge 62 may have the same relative shape as the first material cut edge 60 such that the fringe 74 extends beyond the first material cut edge 60 by a uniform amount along substantially the entire width 70 of the front waist relief area 56 and/or back waist relief area 58. For example, FIG. 4 representatively illustrates a second cut edge 62 and first cut edge 60 defining a fringe 74 that extends beyond the first material cut edge 60 by a uniform amount along substantially the entire width of the front waist relief area 56.

In some embodiments, the second material cut edge 62 may have a different relative shape as compared to the first material cut edge 60 such that the fringe 74 extends beyond the first material cut edge 60 by different amounts along the width 70 of the front waist relief area 56 and/or the back waist relief area 58. For example, FIG. 3 representatively illustrates a second cut edge 62 having a straight shape and a first cut edge 60 having an arcuate shape. This combination of shapes results in a fringe 74 that extends beyond the first material cut edge 60 by a greater distance as measured near the longitudinal centerline as compared to the distance as measured near the intersection of the first material cut edge 60 and the front waist edge 48.

Figure 8:
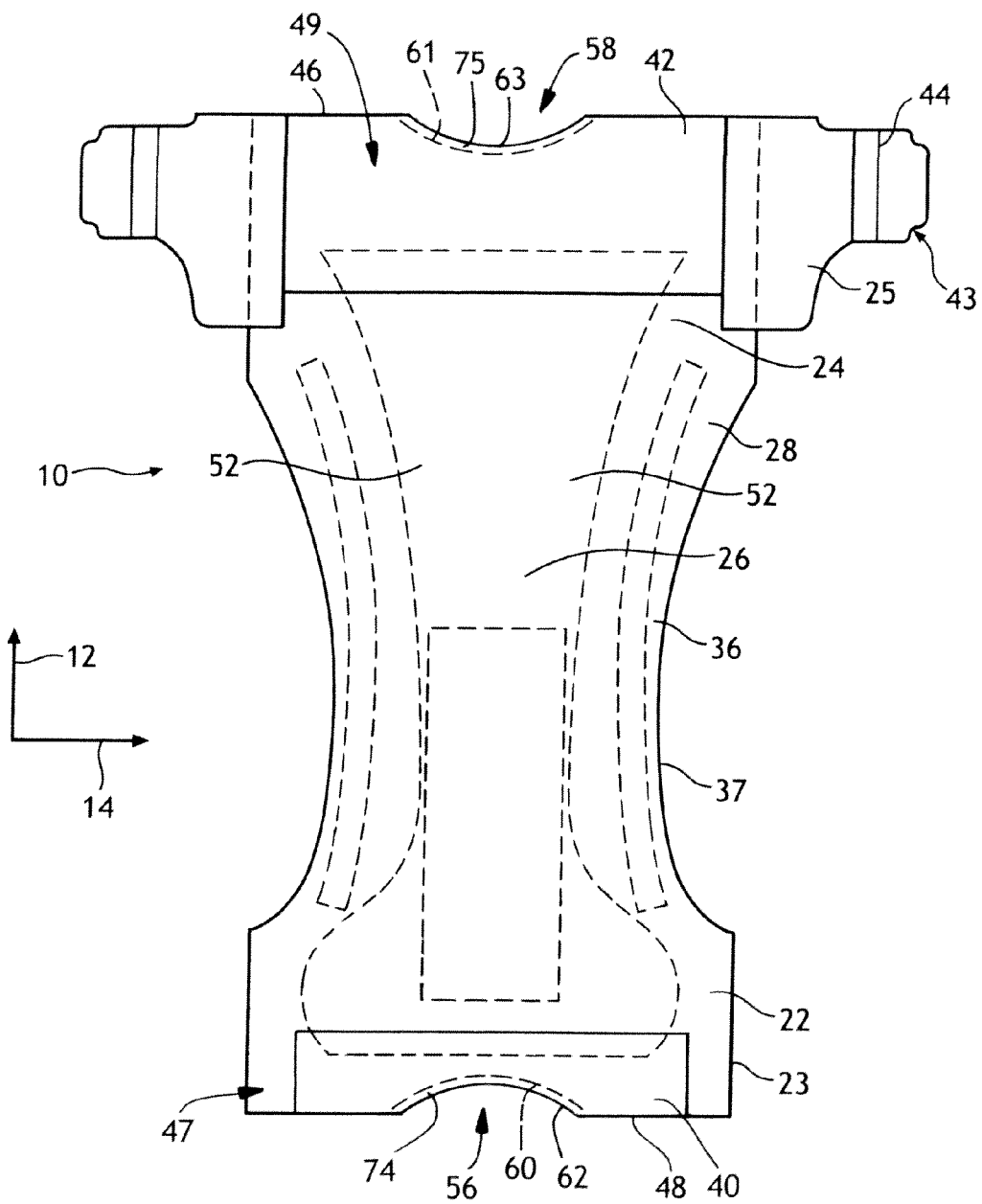

In various embodiments, the absorbent article 10 may include a front waist relief area 56 and a back waist relief area 58. For example, as illustrated in FIG. 8, an absorbent article 10 is illustrated in an unfastened condition. The surface of the diaper 10 which contacts the wearer is facing the viewer in this illustration. The diaper 10 of FIG. 8 includes a front waist relief area 56 defined in part by a first material front cut edge 60 and a second material front cut edge 62 wherein the first material is the outer cover 32 and the second material is the front waist elastic 40. Likewise, the diaper 10 includes a back waist relief area 58 defined in part by a first material back cut edge 61 and a second material back cut edge 63 wherein the first material is the outer cover 32 and the second material is the back waist elastic 42. In the illustrated embodiment, the second material front cut edge 62 of the front waist elastic 40 extends beyond the first material front cut edge 60 of the outer cover 32 to create a front fringe 74 and the second material back cut edge 63 of the back waist elastic 42 extends beyond the first material back cut edge 61 of the outer cover 32 to create a back fringe 75.

Figure 9:
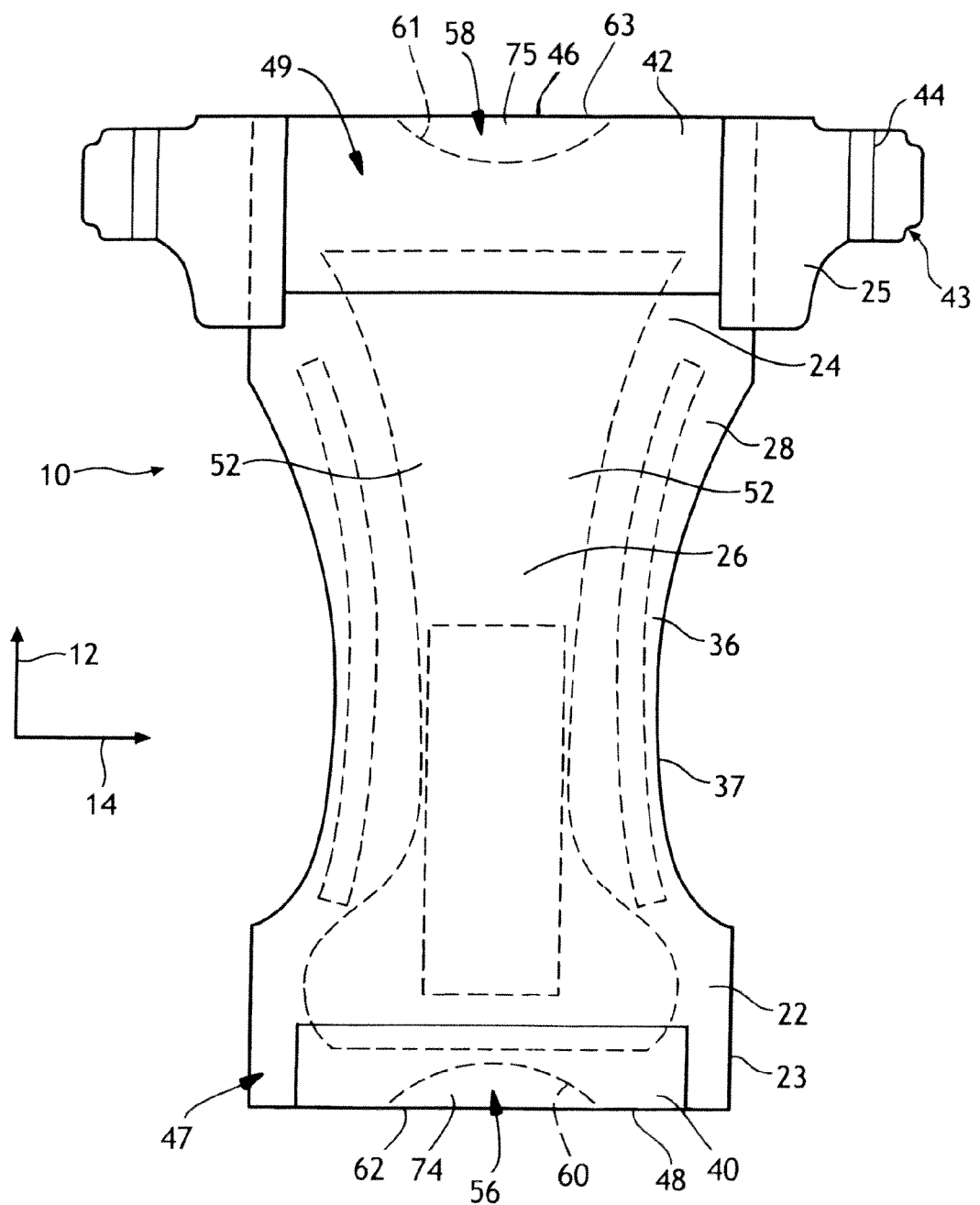

In some embodiments, the second material front cut edge 62 may also include the bodyside liner 30. In these embodiments, the front waist elastic 40 and the bodyside liner 30 would both extend beyond the first material front cut edge 60 of the outer cover 32 to define the front fringe 74 in the front waist relief area 56. Likewise, the back waist elastic 42 and the bodyside liner 30 would both extend beyond the first material back cut edge 61 of the outer cover 32 to define the back fringe 75 in the back waist relief area 58. In yet other embodiments, the second material front cut edge 62 of the front waist elastic 40 may extend all the way to the front waist edge 48 and the second material back cut edge 63 of the back waist elastic 42 may extend all the way to the back waist edge 46 as illustrated in FIG. 9.

Figure 9A:
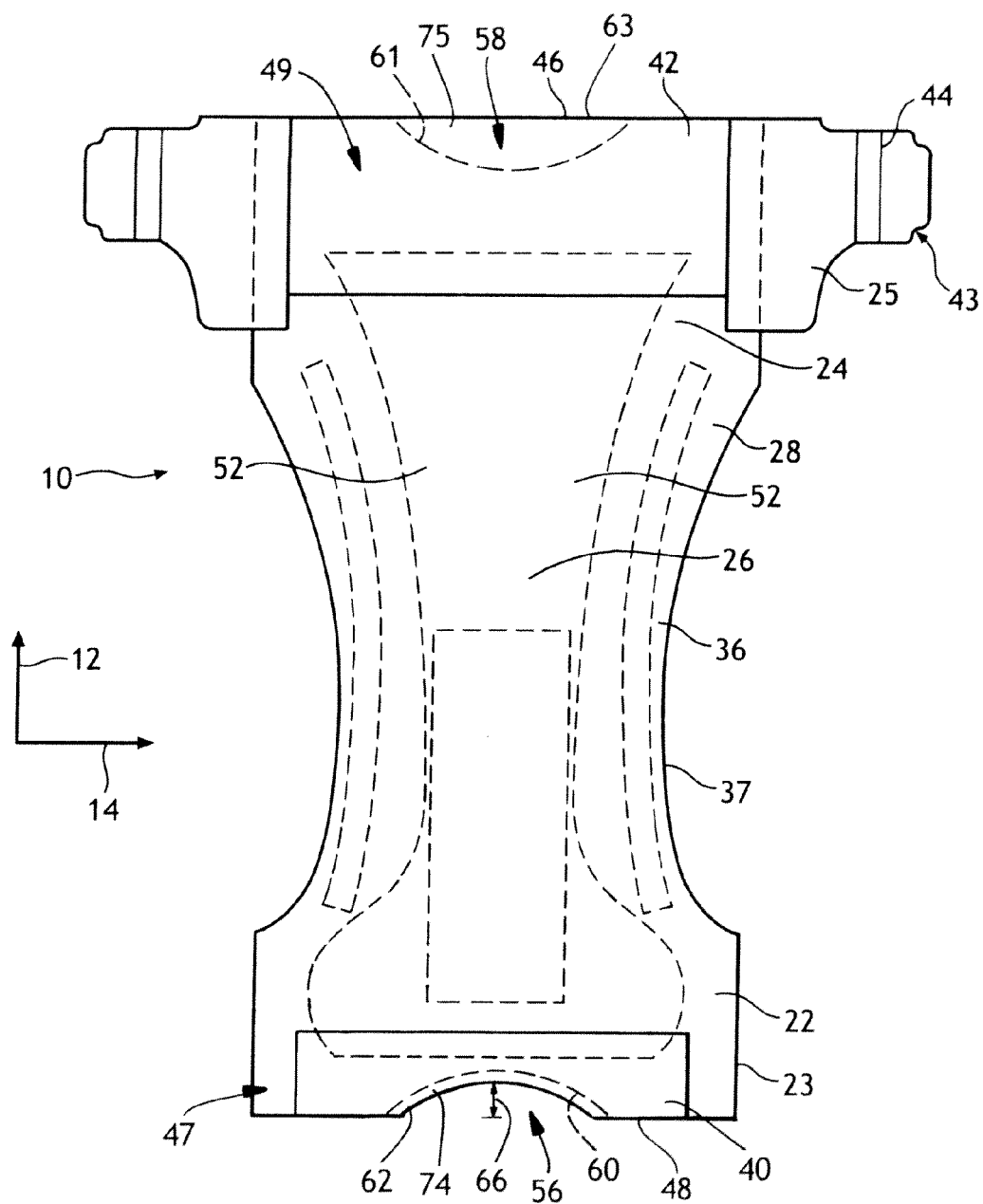

In some embodiments, the second material front cut edge 62 may extend beyond the first material front cut edge 60 to define the front fringe 74 in the front waist relief area 56 while the second material back cut edge 63 of the back waist relief area 58 may extend all the way to the back waist edge 46 as illustrated in FIG. 9A. Referring to FIG. 9A, the front waist elastic 40 extends beyond the first material front cut edge 60 of the outer cover 32 to define the front fringe 74 in the front waist relief area 56. The front waist elastic 40 has a relief depth 66 of greater than zero mm illustrated in this embodiment. The back waist elastic 42 of FIG. 9A extends beyond the first material back cut edge 61 of the outer cover 32 in the back waist relief area 58 to define the back fringe 75. The second material back cut edge 63 of the back waist elastic 42 extends all the way to the back waist edge 46.

Figure 10:
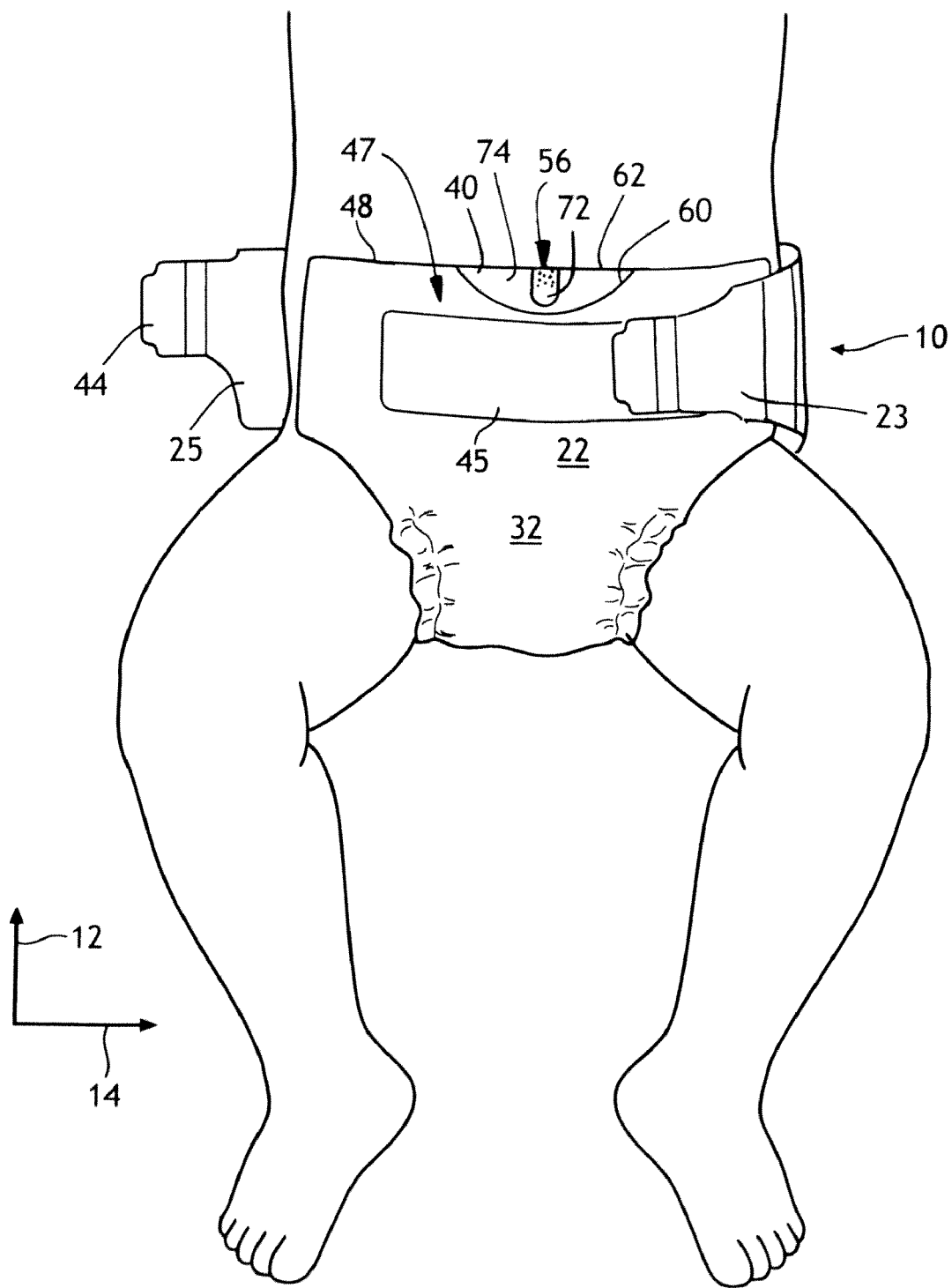
Figure 11:
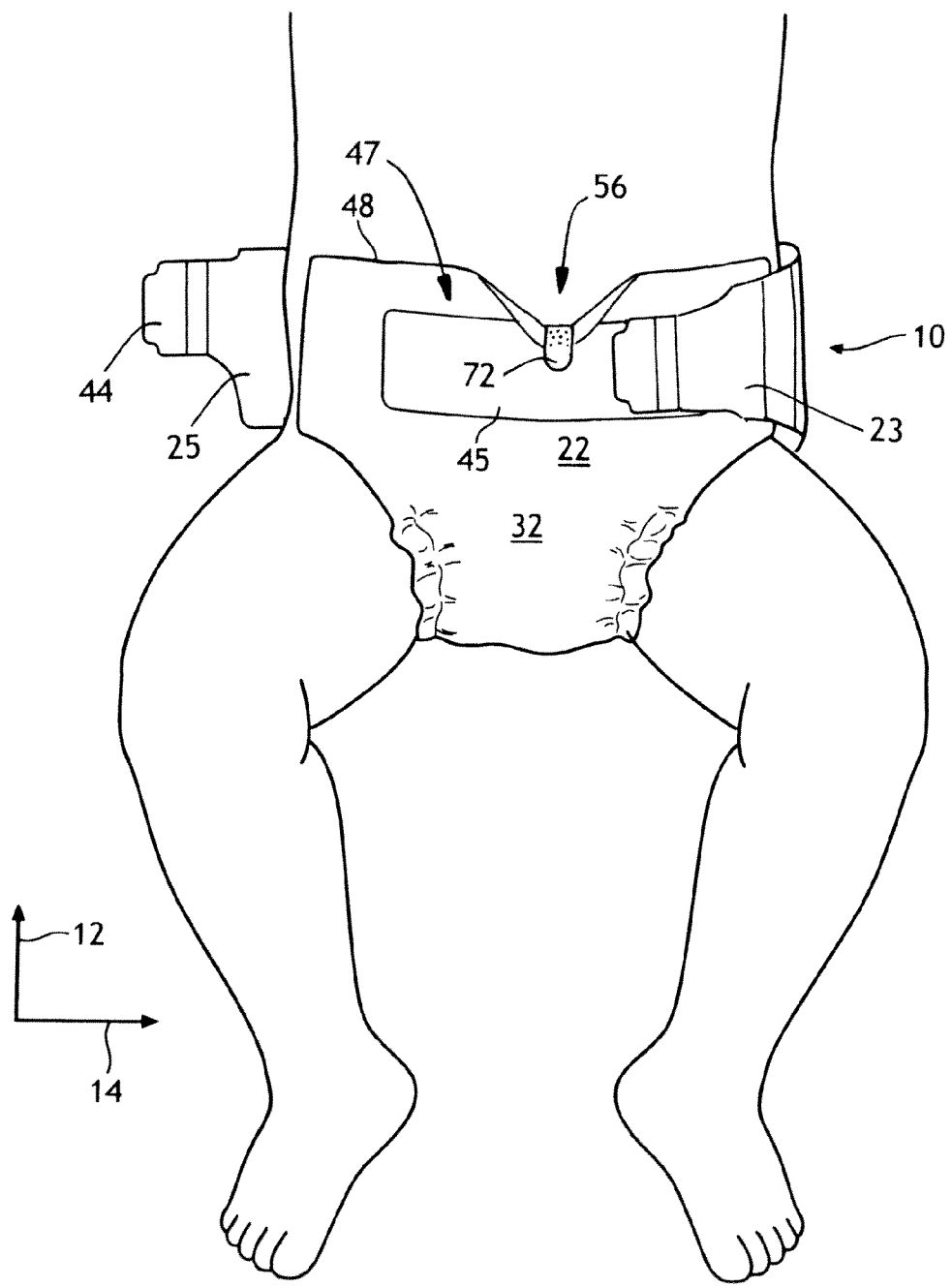

In some embodiments, the fringe 74 may include an anchor tab 72 joined thereto. For example, as illustrated in FIG. 10, a diaper 10 includes a front waist relief area 56 defined in part by a first material cut edge 60 and a second material cut edge 62. The first material includes the outer cover 32 and the second material includes the front waist elastic 40. The cut edge 62 of the front waist elastic 40 extends beyond the cut edge 60 of the outer cover 32 to create a fringe 74. The diaper 10 includes an anchor tab 72 joined to the fringe 74. The anchor tab 72 is provided as an optional feature on some embodiments to allow a user or caregiver to deflect the fringe 74 away from the front waist edge 48 and anchor the fringe 74 in a position that maintains the deflection of the fringe 74. For example, FIG. 11 illustrates the diaper 10 of FIG. 10 wherein the anchor tab 72 has been joined with the front fastener 45 to maintain the fringe 74 in a deflected position.

The diapers 10 of the various embodiments of the present invention may be manufactured by any suitable apparatus and/or method. In some embodiments, a method of making an absorbent article with a waist relief area includes the steps of providing a first web of material moving in a machine direction; cutting a plurality of first relief holes in the first web of material; at least partially covering the plurality of first relief holes with an overlay material; and cutting the web of material in a cross-machine direction to define a plurality of discrete absorbent articles wherein the cross-machine cut extends at least partially through each first relief hole. The resulting discrete absorbent articles include one or more waist relief areas corresponding to the location of the relief holes.

Figure 12:
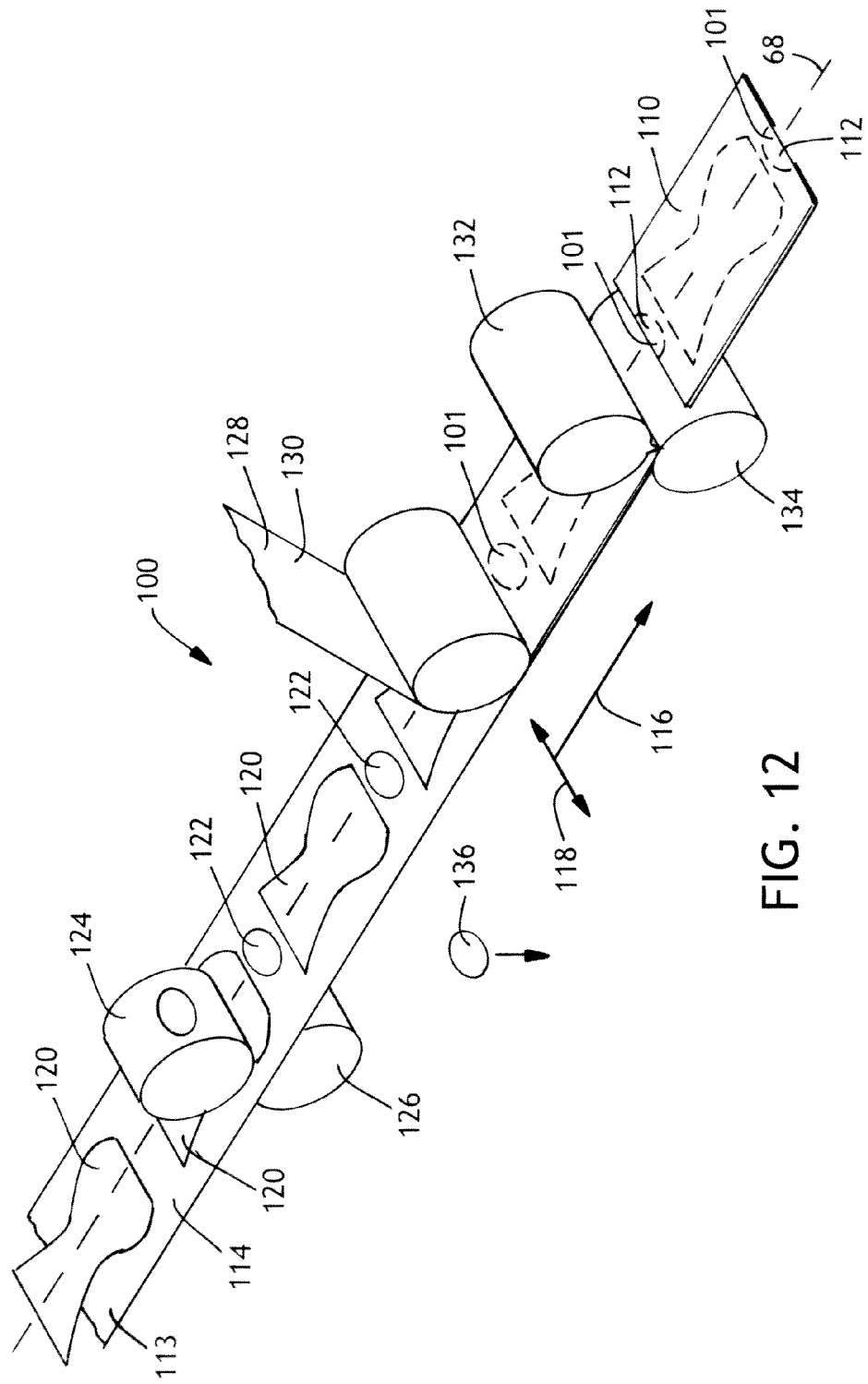
FIGS. 12-17 representatively illustrate perspective views of exemplary embodiments of the methods of the present invention.

For example, FIG. 12 representatively illustrates a method 100 of making absorbent articles 110 with waist relief areas 112. The method 100 includes providing a first web of material 113, such as a web of outer cover material 114, moving in a machine direction 116. As used herein, the direction perpendicular to the machine direction 116 will be referred to as the cross-machine direction 118.

In various embodiments, the method may also include providing a plurality of absorbent cores 120. In the illustrated embodiments, the absorbent cores 120 are illustrated as discrete shaped pads being placed on the web of outer cover material 114. However, the absorbent cores 120 may be provided as discrete units or may be provided as a continuous web of interconnected cores or combinations thereof. Likewise, the absorbent cores 120 may have any suitable shape, composition, or construction as is known in the art. Additionally, the absorbent cores 120 may be introduced into the absorbent article at any suitable position.

The method 100 may further include creating a plurality of first relief holes 122 in the web of outer cover material 114. As illustrated in FIG. 12, the first relief holes 122 may be cut using a rotating die roll 124 in cooperation with a rotating anvil roll 126 to separate a plurality of oval-shaped relief hole trim pieces 136.

The first relief holes 122 may be created using any suitable method and apparatus. For example, the first relief holes 122 may be cut using high pressure water, die cutters, ultrasonic cutters, and the like, and combinations thereof. The first relief holes 122 and/or the second relief holes 146 may have any suitable shape and any suitable orientation. For example, the first relief holes 122 and/or the second relief holes 146 may be generally oval in shape, circular in shape, triangular in shape, diamond-shaped, or shaped like the letter "D" (D-shaped). The first relief holes 122, as illustrated in FIG. 12, have an oval shape with the longer axis oriented in the cross-machine direction 118.

The method 100 also includes the step of at least partially covering the plurality of first relief holes 122 with an overlay material 128. The overlay material 128 may be any suitable material or materials. For example, the overlay material may be the bodyside liner, the front waist elastic, the back waist elastic, the front fastener material, the outer cover facing material, or the like, or combinations thereof. In the embodiment illustrated in FIG. 12, the overlay material 128 is a bodyside liner 130.

The overlay material 128 may completely cover the plurality of first relief holes 122, as illustrated in FIG. 12, or may only partially cover the first relief holes 122. The portion of the overlay material 128 spanning the first relief holes 122 defines a fringe 101. In various embodiments, the overlay material 128 may also cover any other suitable component of the absorbent article 110. For example, the overlay material 128 (bodyside liner 130) of FIG. 12 overlays the outer cover 114, the absorbent cores 120, and the first relief holes 122.

The method 100 also includes the step of cutting the web of outer cover material 114 in the cross-machine direction 118 to define a plurality of discrete absorbent articles 110 wherein each cut extends at least partially through each first relief hole 122. For example, FIG. 12 illustrates a cutoff roll 132 working in conjunction with an anvil roll 134 to cut the web of outer cover material 114 and the web of bodyside liner material 130 in the cross machine direction 118 to define a plurality of discrete absorbent articles 110. The cut extends through the first relief holes 122 to create waist relief areas 112 having a fringe 101 in the discrete absorbent articles 110. In various embodiments, the cutting step may be performed with any suitable method or apparatus.

In some embodiments, the method of making absorbent articles with a waist relief area may include at least partially covering the plurality of first relief holes with a plurality of discrete overlay materials. In various embodiments, the discrete overlay materials may have elasticity in the cross-machine direction 118 and/or the machine direction 116.

Figure 13:
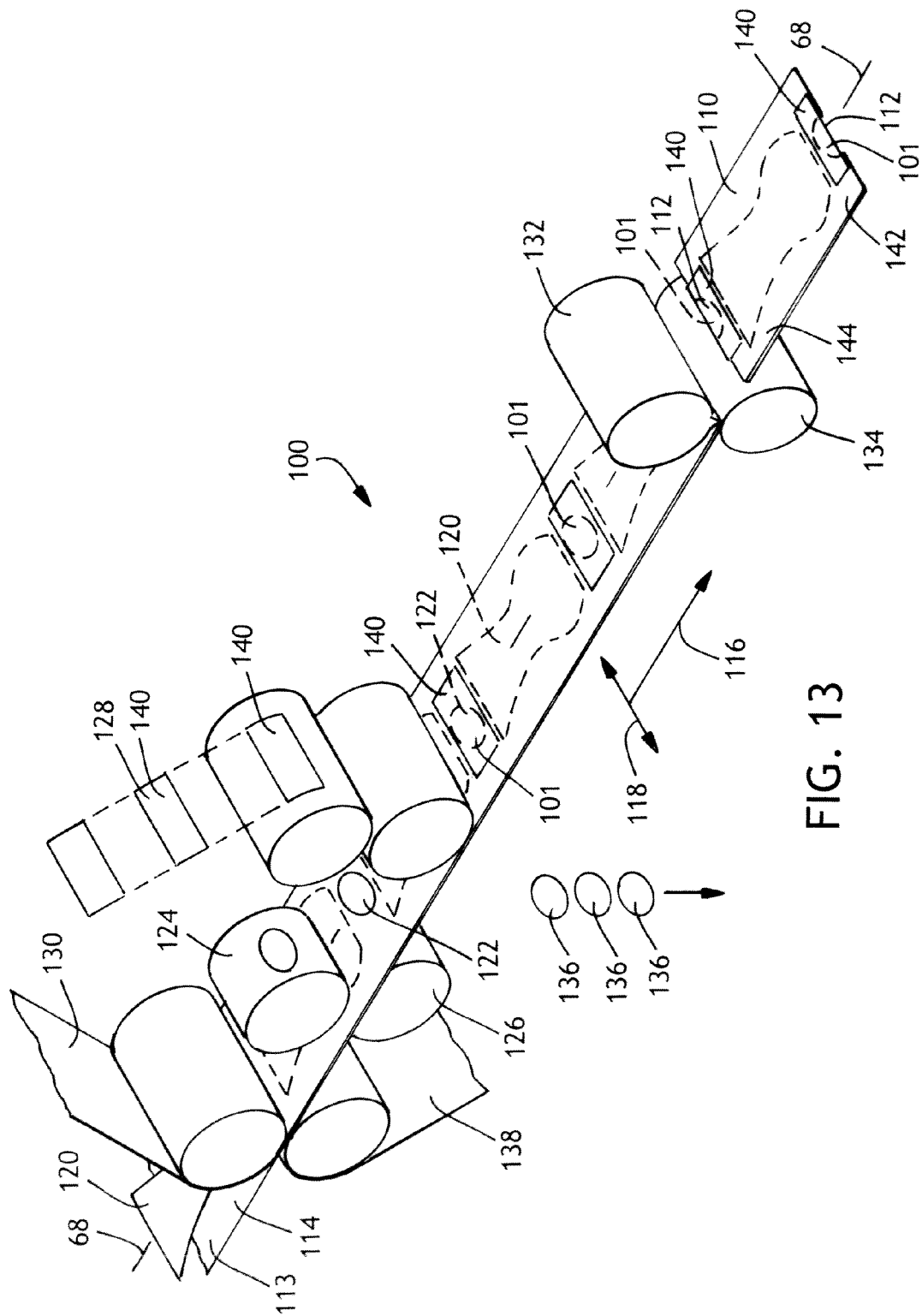

For example, FIG. 13 representatively illustrates a method 100 of making absorbent articles 110 with waist relief areas 112. The method 100 includes providing a first web of material 113, such as a web of outer cover material 114, moving in a machine direction 116. The method may also include providing a plurality of discrete absorbent cores 120 on the web of outer cover material 114. The method may also include additional web materials. For example, the embodiment of FIG. 13 illustrates a bodyside liner material 130 being added in facing relation with the outer cover material 114 with the absorbent cores 120 located therebetween. Optionally, in some embodiments, an outer cover facing material 138 may be joined with the outer cover material to provide a cloth-like feel as is known in the art.

The method 100 of FIG. 13 further includes creating a plurality of first relief holes 122 in the web of outer cover material 114, the web of liner material 130, and the web of outer cover facing material 138. The first relief holes 122 may be cut using a rotating die roll 124 in cooperation with a rotating anvil roll 126 to separate a plurality of oval-shaped relief hole trim pieces 136.

The method 100 also includes the step of at least partially covering the plurality of first relief holes 122 with an overlay material 128. In this embodiment, the overlay materials 128 are discrete waist elastics 140. The discrete waist elastics 140 may completely cover the plurality of first relief holes 122, as illustrated in FIG. 13, or may only partially cover the first relief holes 122. The portions of the discrete waist elastics 140 spanning the first relief holes 122 define a fringe 101.

The method 100 also includes the step of cutting the web of outer cover material 114, bodyside liner material 130, and outer cover facing material 138 in the cross-machine direction 118 to define a plurality of discrete absorbent articles 110 wherein each cut extends at least partially through each first relief hole 122 to create waist relief areas 112 having a fringe 101 in the discrete absorbent articles 110. The cutting step may also sever the discrete waist elastics 140 such that a portion of the discrete waist elastic remains in a front portion 142 of the absorbent article 110 and a portion of the discrete waist elastic remains in a back portion 144. The cutting step may be phased to create waist relief areas 112 in the front portion 142 of the absorbent article 110, in the back portion 144 of the absorbent article 110, or both the front portion 142 and the back portion 144, as illustrated.

Figure 14:
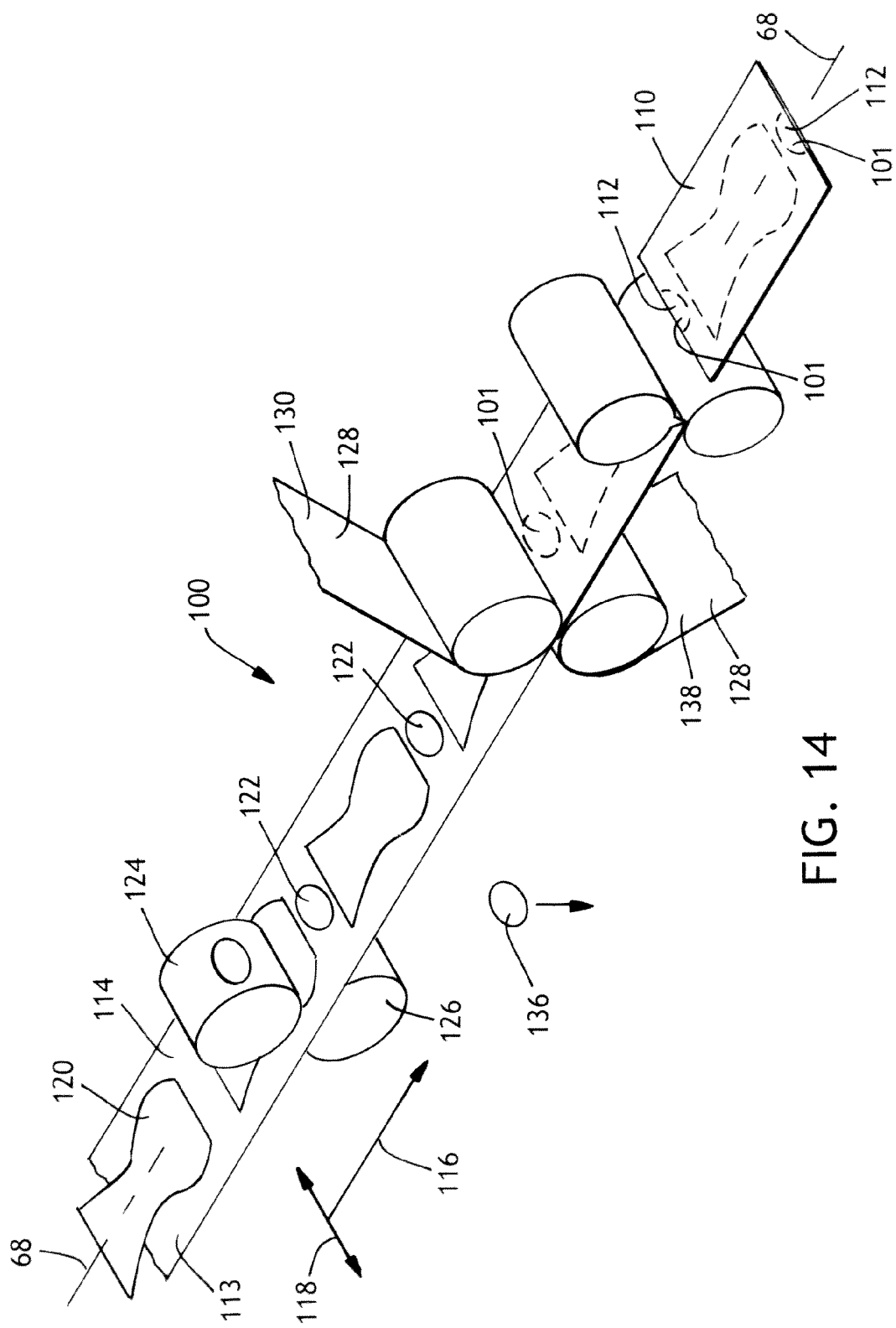

In some embodiments, the plurality of first relief holes 156 may be covered with a web of outer cover facing material 138 and the cutting step may include cutting the outer cover facing material 138 in the cross-machine direction 118. For example, FIG. 14 representatively illustrates a method 100 of making absorbent articles 110 with waist relief areas 112. The method 100 includes providing a first web of material 113, such as a web of outer cover material 114, moving in a machine direction 116. The method 100 also includes providing a plurality of discrete absorbent cores 120 on the web of outer cover material 114. The method 100 of FIG. 14 further includes creating a plurality of first relief holes 122 in the web of outer cover material 114. The first relief holes 122 may be cut using a rotating die roll 124 in cooperation with a rotating anvil roll 126 to separate a plurality of oval-shaped relief hole trim pieces 136.

The method 100 also includes the step of at least partially covering the plurality of first relief holes 122 with one or more overlay materials 128. The embodiment of FIG. 14 illustrates a bodyside liner material 130 being added in facing relation with the outer cover material 114 wherein the absorbent cores 120 are located therebetween. Additionally, an outer cover facing material 138 is joined with the outer cover material 114. Thus, in this embodiment, the overlay materials 128 are the bodyside liner material 130 and the outer cover facing material 138. The overlay materials 128 completely cover the plurality of first relief holes 122. The portion of the overly materials 128 that span the first relief holes 122 define a fringe 101.

The method 100 also includes the step of cutting the web of outer cover material 114, the bodyside liner material 130, and outer cover facing material 138 in the cross-machine direction 118 to define a plurality of discrete absorbent articles 110 wherein each cut extends at least partially through each first relief hole 122 to create waist relief areas 112 in the discrete absorbent articles 110. The cutting step may be phased to create waist relief areas 112 having a fringe 101 in the front portion 142 of the absorbent article 110, in the back portion 144 of the absorbent article 110, or both the front portion 142 and the back portion 144, as illustrated.

Figure 15:
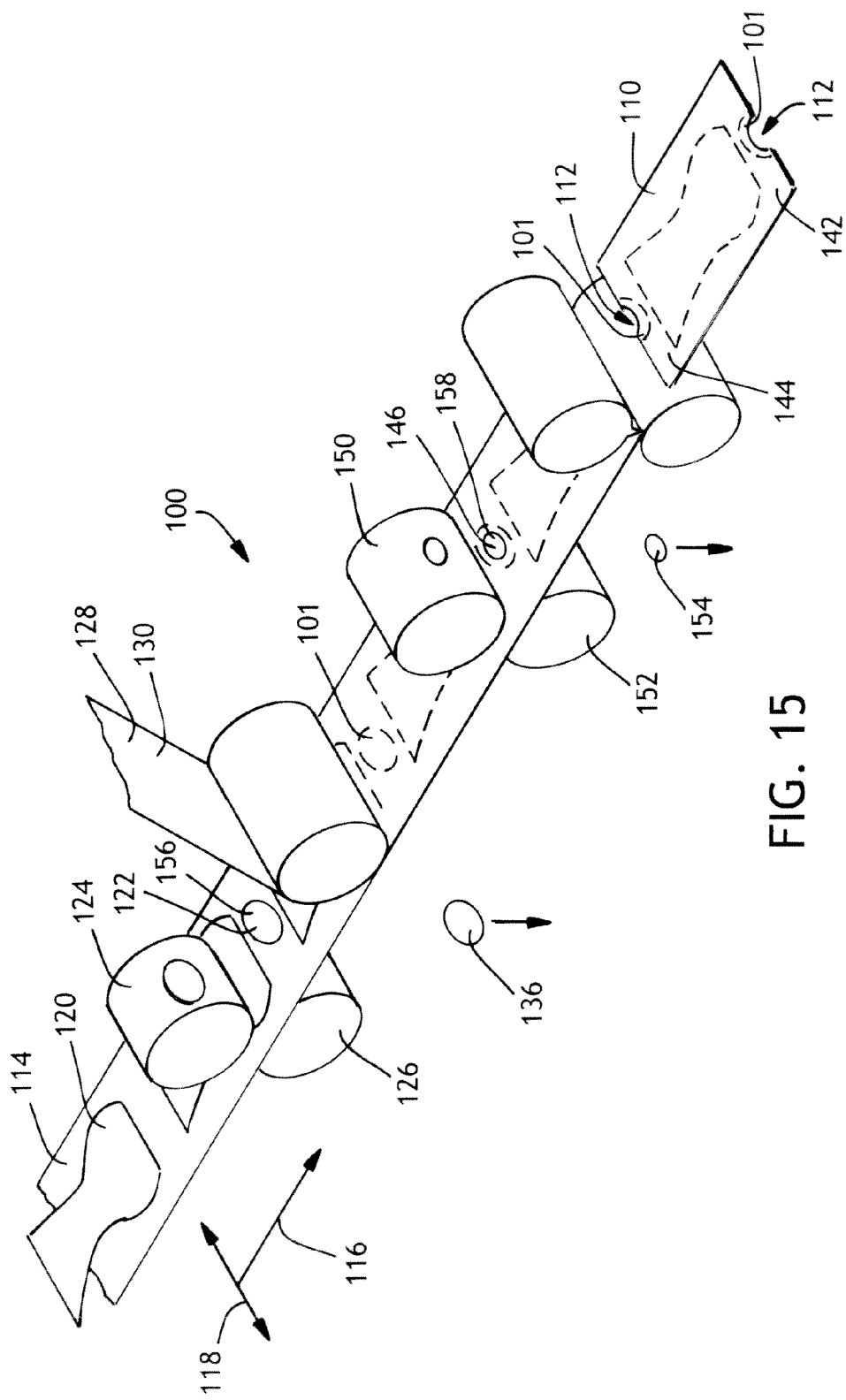

Referring now to FIG. 15, a method 100 of making an absorbent article 110 with a waist relief area 112 is illustrated. The method 100 may include providing a first web of material 113, such as a web of outer cover material 114, moving in a machine direction 116. The method 110 may further include a plurality of discrete absorbent cores 120 spaced and placed upon the web of outer cover material 114. The method further includes cutting a plurality of first relief holes 122 in the web of outer cover material 114. The first relief holes 122 may be cut using a rotating die roll 124 in cooperation with a rotating knife anvil roll 126 to separate a plurality of oval-shaped relief hole trim pieces 136.

The method 100 further includes covering the plurality of first relief holes 122 with an overlay material 128, such as bodyside liner 130. The portion of the bodyside liner 130 that spans the first relief holes 122 defines a fringe 101. The method 100 continues with cutting a plurality of second relief holes 146 in at least a portion of the overlay material 128 spanning the first relief holes (i.e., the fringe 101) using a second rotating die roll 150 in cooperation with a second rotating anvil roll 152 to separate a plurality of oval-shaped relief hole trim pieces 154. The web of outer cover material 114 and the web of liner material 130 are cut in the cross-machine direction 118 to define a plurality of discrete absorbent articles 110. Each cross-machine cut extends at least partially through each first relief hole 122 and each second relief hole 146 to create waist relief areas 112 with fringe 101 in the front portion 142, back portion 144, or both the front portion 142 and the back portion 144 as illustrated.

In various embodiments, each of the second relief holes 146 may be registered within each of the first relief holes 122 as illustrated in FIG. 15. In some embodiments, the second relief holes 146 may be centered in the first relief holes 122 relative to the machine direction 116, the cross machine direction 118, or both as illustrated in FIG. 15. In various embodiments, each of the first relief holes 122 define a first relief hole area 156 and each of the second relief holes 146 define a second relief hole area 158 less than the first relief hole area 156 as illustrated in FIG. 15. As such, at least a portion of the fringe 101 remains in the waist relief areas 112 of the absorbent articles 110.

Figure 16:
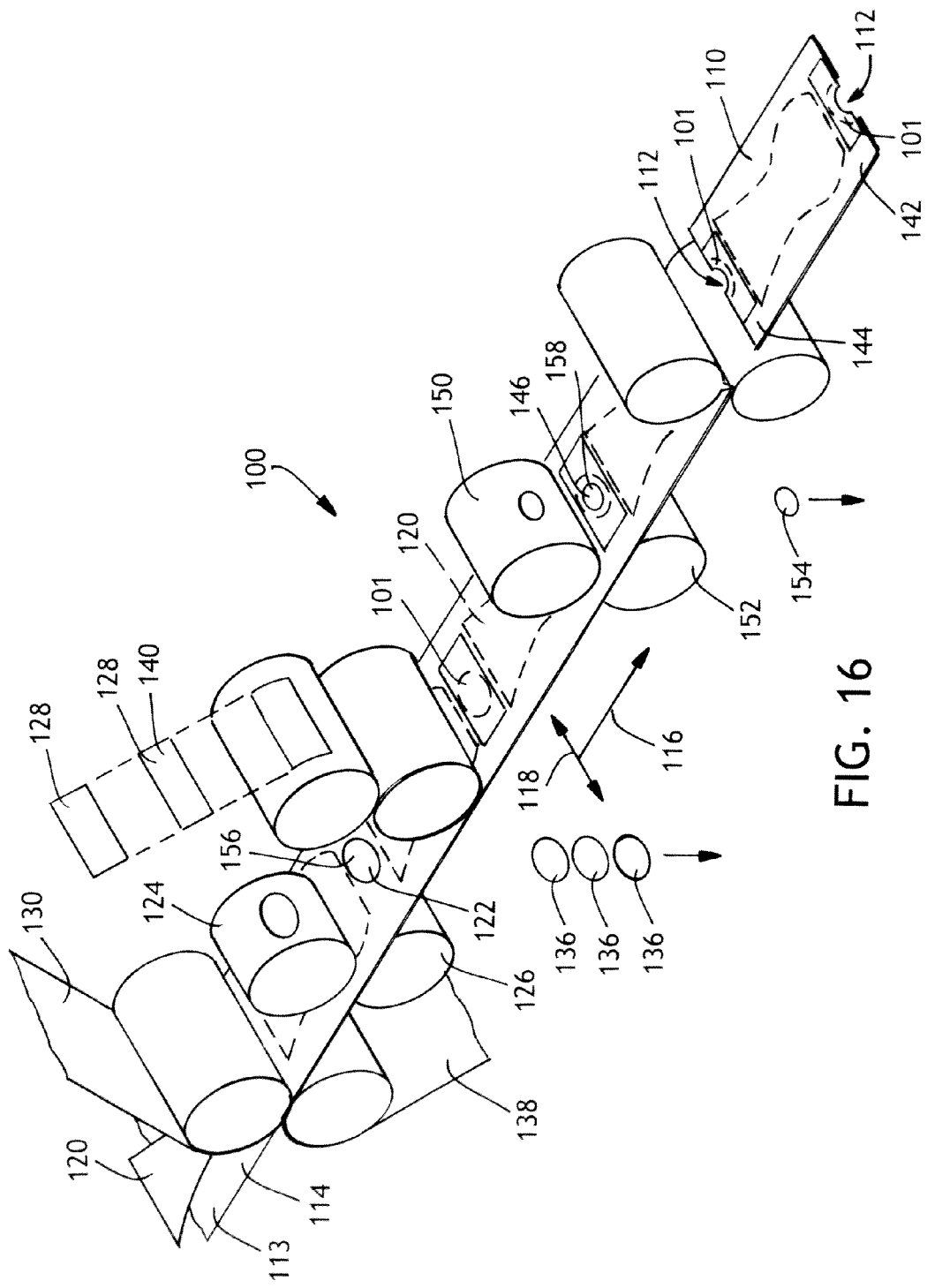

In some embodiments, the overlay material 128 may be a plurality of discrete waistbands having elasticity in the cross machine direction 118. For example FIG. 16 representatively illustrates a method 100 of making an absorbent article 110 with waist relief areas 112. The method 100 includes providing a first web of material 113, such as a web of outer cover material 114, moving in a machine direction 116. The method 110 further includes providing a plurality of discrete absorbent cores 120 spaced and placed upon the web of outer cover material 114. The absorbent cores 120 are positioned between the outer cover material 114 and a bodyside liner material 130. Optionally, an outer cover facing material 138 may be joined with the outer cover material 114. The method further includes cutting a plurality of first relief holes 122 in the web of outer cover material 114, the bodyside liner material 130, and the outer cover facing material 138. The first relief holes 122 may be cut using a rotating die roll 124 in cooperation with a rotating knife anvil roll 126 to separate a plurality of oval-shaped relief hole trim pieces 136.

The method 100 further includes covering the plurality of first relief holes 122 with an overlay material 128, such as plurality of discrete waist elastic material 140. The portion of the waist material 140 spanning the first relief holes 122 defines a fringe 101. The method 100 continues with cutting a plurality of second relief holes 146 in at least a portion of the overlay material 128 spanning the first relief holes (i.e. the fringe 101) using a second rotating die roll 150 in cooperation with a second rotating anvil roll 152 to separate a plurality of oval-shaped relief hole trim pieces 154. The web of outer cover material 114, the web of liner material 130, the web of outer cover facing material 138, and the discrete waist elastic material 140 are cut in the cross-machine direction 118 to define a plurality of discrete absorbent articles 110. Each cross-machine cut extends at least partially through each first relief hole 122 and each second relief hole 146 to create waist relief areas 112 with fringe 101 in the front portion 142, back portion 144, or both the front portion 142 and the back portion 144 as illustrated. The second relief holes 146 are registered within each of the first relief holes 122 as illustrated in FIG. 15. Additionally, the second relief holes 146 are centered in the first relief holes 122 relative to both the machine direction 116 and the cross-machine direction 118 as illustrated in FIG. 15. Each of the first relief holes define a first relief hole area 156 and each of the second relief holes define a second relief hole area 158 less than the first relief hole area 156 thereby leaving some fringe 101 in the absorbent article 110 as illustrated in FIG. 16.

Figure 17:
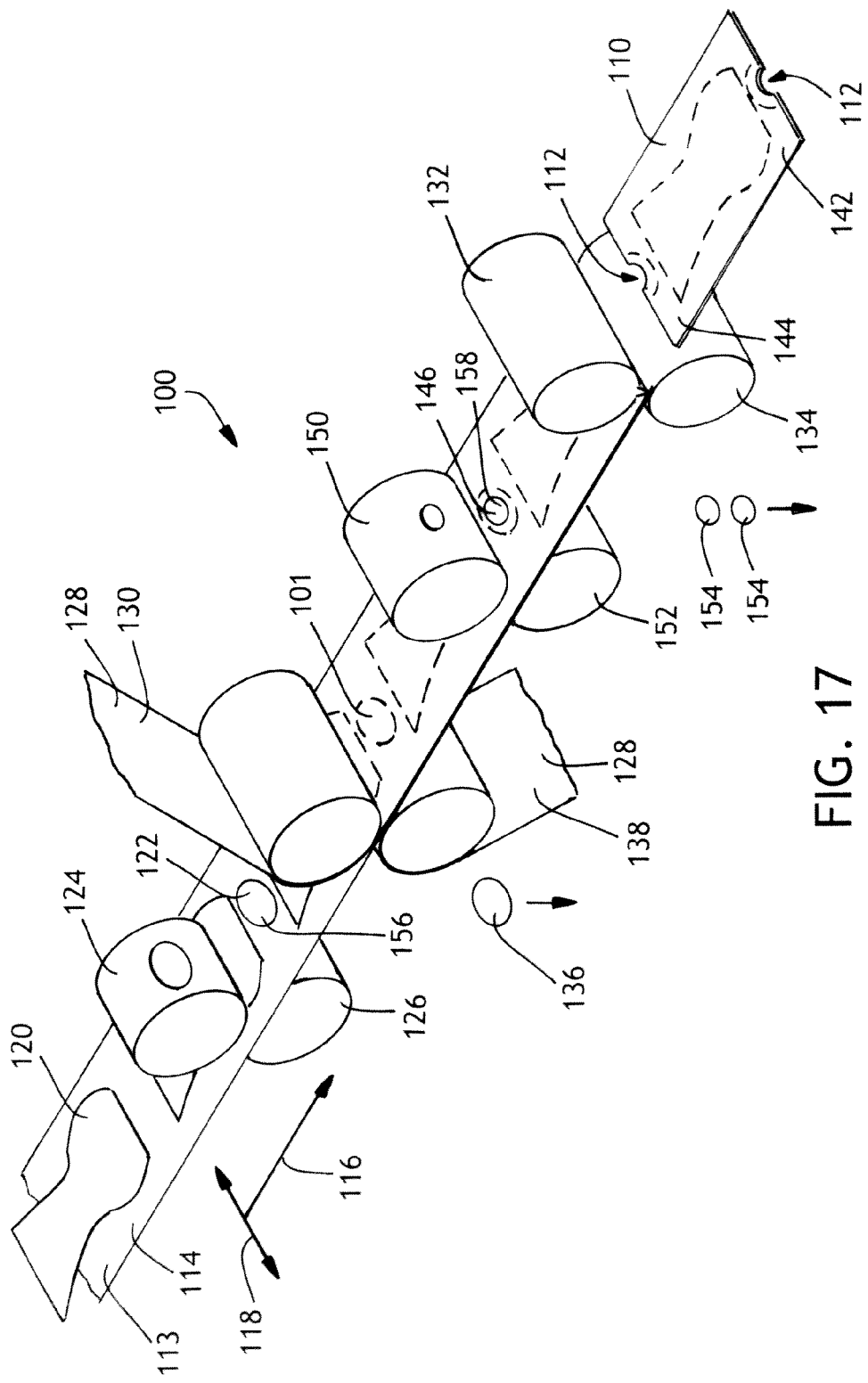

FIG. 17 representatively illustrates a method 100 of making an absorbent article 110 with waist relief areas 112. The method 100 includes providing a first web 113, such as a web of outer cover material 114, moving in a machine direction 116. The method 110 further includes providing a plurality of discrete absorbent cores 120 spaced and placed upon the web of outer cover material 114. The method further includes cutting a plurality of first relief holes 122 in the web of outer cover material 114. The first relief holes 122 may be cut using a rotating die roll 124 in cooperation with a rotating knife anvil roll 126 to separate a plurality of oval-shaped relief hole trim pieces 136.

The method 100 further includes covering the plurality of first relief holes 122 with two overlay materials 128, such as bodyside liner material 130 and outer cover facing material 138. The portions of the bodyside liner material 130 and outer cover facing material 138 overlying the first relief holes 122 define a fringe 101. The method 100 continues with cutting a plurality of second relief holes 146 in at least a portion of the overlay materials 128 spanning the first relief holes (i.e., the fringe 101) using a second rotating die roll 150 in cooperation with a second rotating anvil roll 152 to separate a plurality of oval-shaped relief hole trim pieces 154. The web of outer cover material 114, the web of liner material 130, and the web of outer cover facing material 138 are cut in the cross-machine direction 118 to define a plurality of discrete absorbent articles 110. Each cross-machine cut extends at least partially through each first relief hole 122 and each second relief hole 146 to create waist relief areas 112 with fringe 101 in the front portion 142, back portion 144, or both the front portion 142 and the back portion 144 as illustrated. The second relief holes 146 are registered within each of the first relief holes 122 as illustrated. Additionally, the second relief holes 146 are centered in the first relief holes 122 relative to both the machine direction 116 and the cross-machine direction 118. Each of the first relief holes define a first relief hole area 156 and each of the second relief holes define a second relief hole area 158 less than the first relief hole area 156 thereby leaving some fringe 101 in the waist relief areas 112 of the absorbent articles 110 as illustrated.

The method of the present invention may include creating any suitable shape for the first relief holes 122 and/or the second relief holes 146. The method of the present invention may include any suitable relative size between the first relief holes 122 and the second relief holes 146. For example, the first relief holes 122 may have a first relief hole area 156 and the second relief holes 146 may have a second relief hole area 158 that is less than the first relief hole area 156.

The method of the present invention may also include any suitable combination of phasing of the first relief holes 122 and/or the second relief holes 146 relative to the position of the front waist edge 48 and/or back waist edge 46. For example, in some embodiments, the first relief holes 122 and/or the second relief holes 146 may be phased such that they are predominately in the front waist portion 47, predominately in the back waist region 49, or substantially equal in both the front waist region 47 and the back waist region 49. In some embodiments, the cutting step may be phased to provide at least 90% of the second relief hole area 158 in the front waist region 47 of the discrete absorbent articles 10 and less than 10% of the second relief hole area 158 in the back waist region 49. In some embodiments, the method may further include phasing to provide at least ¼ the first relief hole area 156 in a front waist region 47 and at least ¼ the first relief hole area 156 in the back waist region 49 of the discrete absorbent articles 10.

Figure 18:
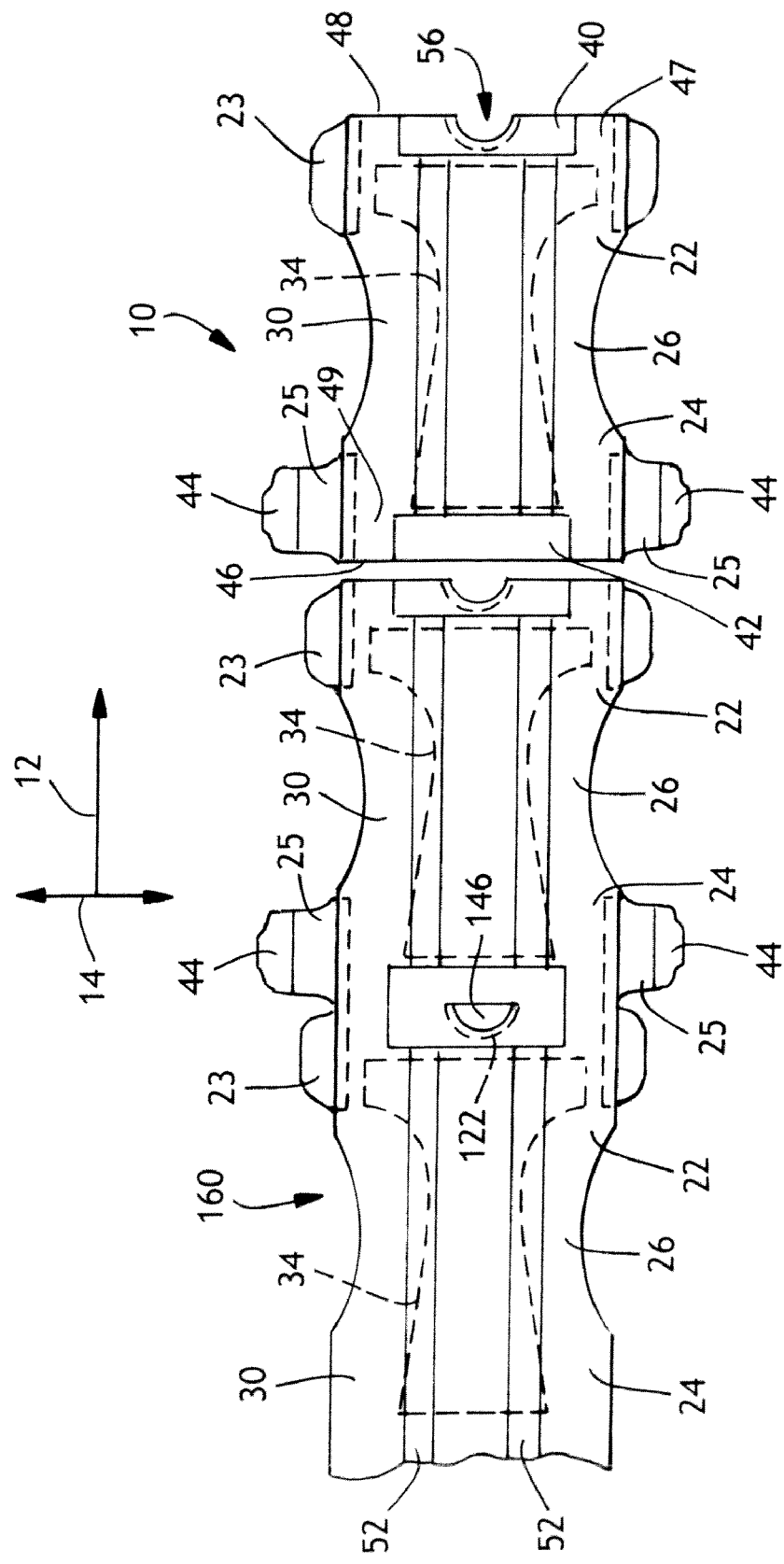
FIGS. 18-19 representatively illustrate top plan views of exemplary embodiments of the methods of the present invention.

Referring now to FIG. 18, a top plan view of a portion of an exemplary web before and after being cut into discrete absorbent articles 10 is illustrated. The absorbent articles 10 illustrated in FIG. 18 are exemplary of those described herein and include a front waist relief area 56. In this example, the first relief holes 122 have a D-shape and the second relief holes 146 have a D-shape. Also, in this embodiment, the second relief holes 146 are registered relative to the first relief holes 122 such that the straight portion of the D-shapes are generally aligned. The first relief holes 122 and second relief holes 146 are phased relative to the cut such that 100% of the first relief hole area 156 and 100% of the second relief hole area 158 are in the front waist region 47. In various embodiments, the first relief holes 122 and second relief holes 146 are phased relative to the cut such that at least 95% of the first relief hole area 156 and at least 95% of the second relief hole area 158 are in the front waist region 47. In some embodiments, the first relief holes 122 and second relief holes 146 are phased relative to the cut such that at least 90% of the first relief hole area 156 and at least 90% of the second relief hole area 158 are in the front waist region 47.

Figure 19:
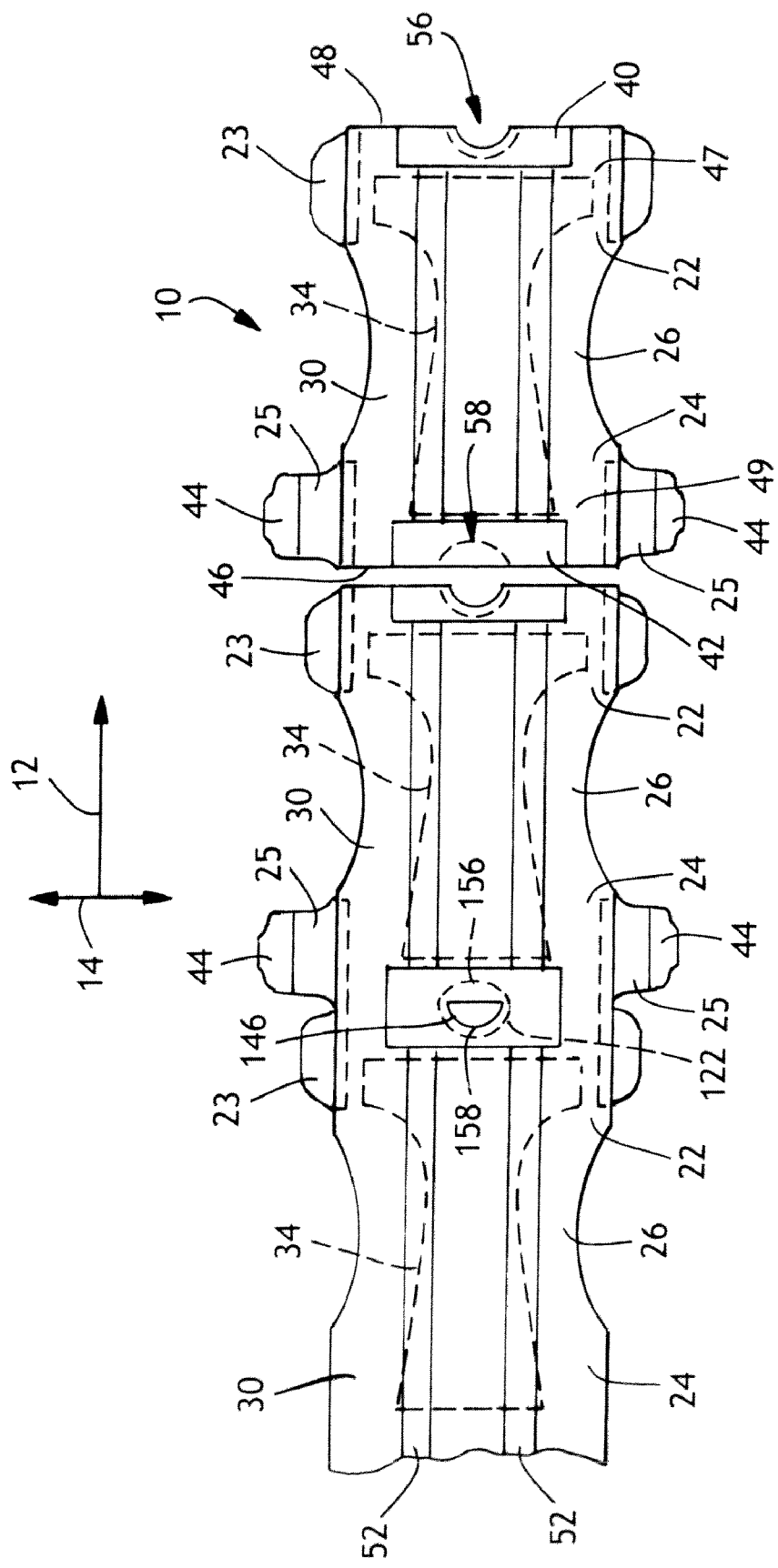

In some embodiments, the first relief holes 122 may have an oval-shape and the second relief holes 146 may have a D-shape. For example, FIG. 19 illustrates an exemplary web before and after being cut into discrete absorbent articles 10. In this embodiment, the first relief holes 122 are phased relative to the cut such that about ½ the first relief hole area 156 is in the front waist region 47 and about ½ the first relief hole area 156 is in the back waist region 49. Likewise, the second relief holes 146 are phased relative to the cut such that 100% of the second relief hole area 158 is in the front waist region 47 and none of the second relief hole area 158 is in the back waist region 49. In some embodiments, the second relief holes 146 are phased relative to the cut such that at least 95% of the second relief hole area 158 is in the front waist region 47 and less than 5% of the second relief hole area 158 is in the back waist region 49. In some embodiments, the second relief holes 146 are phased relative to the cut such that at least 90% of the second relief hole area 158 is in the front waist region 47 and less than 10% of the second relief hole area 158 is in the back waist region 49.

While the invention has been described in detail with respect to specific embodiments thereof, it will be appreciated that those skilled in the art, upon attaining an understanding of the foregoing will readily conceive of alterations to, variations of and equivalents to these embodiments. Accordingly, the scope of the present invention should be assessed as that of the appended claims and any equivalents thereto.

The invention claimed is:

1. An absorbent article comprising,
   a liquid pervious bodyside liner;
   a liquid impervious outer cover;
   an absorbent core positioned between the bodyside liner and the outer cover;
   the absorbent article defining a crotch portion connected between a front portion and a back portion; the front portion includes a front waist region, a front waist edge, and a front waist relief area; the back portion includes a back waist region, a back waist edge, and a back waist relief area;
   the front waist relief area is defined in part by a first material cut edge and a second material cut edge wherein the first material cut edge defines a first relief depth of at least 10 mm and the second material cut edge defines a second relief depth of at least 3 mm less than the first relief depth;
   the back waist relief area is defined in part by a first material back cut edge and a second material back cut edge wherein the first material back cut edge defines a first back relief depth and the second material back cut edge defines a second back relief depth wherein the second back relief depth is at least 3 mm less than the first back relief depth.

2. The absorbent article of claim 1 wherein the first material comprises the outer cover and the second material comprises the liner.

3. The absorbent article of claim 1 wherein the first material comprises the outer cover and the second material comprises a front waist elastic.

4. The absorbent article of claim 1 further comprising an outer cover facing material wherein the first material comprises the outer cover and the second material comprises the outer cover facing material.

5. The absorbent article of claim 1 further comprising a fastener landing material wherein the first material comprises the outer cover and the second material comprises the fastener landing material.

6. The absorbent article of claim 1 wherein the front waist relief area defines a width and the second material cut edge extends beyond the first material cut edge by the same amount along substantially the entire width of the front waist relief area.

7. The absorbent article of claim 1 wherein the first material cut edge defines a first relief depth of least 20 mm and a first relief width of at least 60 mm.

8. The absorbent article of claim 7 wherein the second material cut edge defines a second relief depth of less than 3 mm.

9. The absorbent article of claim 8 wherein the second material cut edge extends beyond the first material cut edge to define a fringe and the fringe includes an anchor tab joined thereto.

10. The absorbent article of claim 1 wherein the front waist relief area defines a width and the second material cut edge extends beyond the first material cut edge by the same amount along substantially the entire width of the front waist relief area and the second material has a second back relief depth of less than 3 mm in the back waist relief area.

11. An absorbent article comprising,
a liquid pervious bodyside liner;
a liquid impervious outer cover;
an absorbent core positioned between the liner and the outer cover;
the absorbent article defining a crotch portion connected between a front portion and a back portion; the front portion includes a front waist region, a front waist edge, and a front waist relief area; the back portion includes a back waist region, a back waist edge, and a back waist relief area:
the front waist relief area is defined in part by a first material front cut edge and a second material front cut edge;
the back waist relief area is defined in part by a first material back cut edge; and a second material back cut edge;
the first material front cut edge has a first front relief depth of a at least 20 mm, the second material front cut edge has a second front relief depth of at least 10 mm, and the second front relief depth is at least 3 mm less than the first front relief depth; the first material back cut edge has a back relief depth of at least 10 mm in the back waist relief area; and
the first material comprises the outer cover and the second material comprises a front waist elastic joined to the front waist region.

12. The absorbent article of claim 11 wherein the front waist relief area defines a width and the second material front cut edge extends beyond the first material front cut edge to define a fringe and wherein the fringe extends beyond the first material front cut edge by the same amount along substantially the entire width of the front waist relief area.

13. The absorbent article of claim 11 wherein the second material back cut edge has a back relief depth of less than 3 mm.

14. The absorbent article of claim 13 wherein the front waist relief area defines a width and the second material front cut edge extends beyond the first material front cut edge by the same amount along substantially the entire width of the front waist relief area.

15. The absorbent article of claim 11 further comprising an outercover facing wherein the second material front cut edge of the front waist elastic extends beyond the first material front cut edge of the outercover, the outercover facing, and the liner.

16. An absorbent article comprising,
a liquid pervious bodyside liner;
a liquid impervious outer cover;
an absorbent core positioned between the liner and the outer cover;
the absorbent article defining a crotch portion connected between a front portion and a back portion; the front portion includes a front waist region, a front waist edge, and a front waist relief area;
the front waist relief area is defined in part by a first material front cut edge and a second material front cut edge;
the back waist relief area is defined in part by the first material back cut edge and the second material back cut edge;
the first material front cut edge has a first front relief depth of at least 20 mm, the second material front cut edge has a second front relief depth of at least 10 mm and the second front relief depth is at least 3 mm less than the first front relief depth;
the first material back cut edge has a first back relief depth of at least 5 mm; and
the first material comprises the outer cover and the second material comprises a waist elastic.

17. The absorbent article of claim 16 wherein the absorbent article defines a longitudinal centerline and wherein the second material front cut edge extends beyond the front cut edge of the outercover, outercover facing, and liner at the longitudinal centerline.

18. The absorbent article of claim 16 wherein the front waist relief area defines a width and wherein the second material front cut edge extends beyond the first material front cut edge to define a front fringe and wherein the front fringe extends beyond the first material front cut edge by the same amount along substantially the entire width of the front waist relief area.

* * * * *